US011565229B2

United States Patent
Steinfeld et al.

(10) Patent No.: US 11,565,229 B2
(45) Date of Patent: Jan. 31, 2023

(54) THERMOCHEMICAL REACTOR SYSTEM FOR A TEMPERATURE SWING CYCLIC PROCESS WITH INTEGRATED HEAT RECOVERY AND A METHOD FOR OPERATING THE SAME

(71) Applicant: ETH Zurich, Zurich (CH)

(72) Inventors: Aldo Steinfeld, Brugg (CH); Philipp Furler, Zurich (CH); Andreas Haselbacher, Forch (CH); Lukas Geissbühler, Bern (CH)

(73) Assignee: ETH Zürich, Zürich (CH)

( * ) Notice: Subject to any disclaimer, the term of this patent is extended or adjusted under 35 U.S.C. 154(b) by 653 days.

(21) Appl. No.: 16/342,262

(22) PCT Filed: Oct. 10, 2017

(86) PCT No.: PCT/EP2017/075804
§ 371 (c)(1),
(2) Date: Apr. 16, 2019

(87) PCT Pub. No.: WO2018/073049
PCT Pub. Date: Apr. 26, 2018

(65) Prior Publication Data
US 2019/0321798 A1    Oct. 24, 2019

(30) Foreign Application Priority Data

Oct. 17, 2016    (EP) .................................... 16194074

(51) Int. Cl.
*B01J 8/00*    (2006.01)
*B01J 8/02*    (2006.01)
(Continued)

(52) U.S. Cl.
CPC ......... *B01J 19/0013* (2013.01); *B01J 19/249* (2013.01); *C01B 3/063* (2013.01);
(Continued)

(58) Field of Classification Search
CPC ......... B01J 8/00; B01J 8/02; B01J 8/06; B01J 8/067; B01J 19/00; B01J 19/0006;
(Continued)

(56) References Cited

U.S. PATENT DOCUMENTS 2,642,381 A * 6/1953 Dickinson .............. C10G 11/10
208/57
2011/0117004 A1   5/2011 Lamont et al.
(Continued)

FOREIGN PATENT DOCUMENTS

EP             2520361 A1     11/2012
WO     WO-2016036242 A1 *   3/2016  .............. F25B 17/08

OTHER PUBLICATIONS

Daniel Marxer, et al., "Demonstration of the Entire Production Chain to Renewable Kerosene via Solar Thermochemical Splitting of H20 and CO2 ," Energy and Fuels, vol. 29, No. 5, pp. 3241-3250, May 21, 2015.
(Continued)

*Primary Examiner* — Natasha E Young
(74) *Attorney, Agent, or Firm* — Henry Patent Law Firm PLLC

(57) ABSTRACT

Disclosed is a thermochemical reactor system and method for a temperature swing cyclic process with integrated heat recovery having at least two modules, wherein each module includes at least one chemical reaction zone and at least one thermal energy storage unit. The at least two modules are operationally connected for at least one heat transfer fluid for transporting heat between the two modules. Each chemical reaction zone includes at least one reacting material that undergoes in a reversible manner an endothermic reaction at temperature $T_{endo}$ and an exothermic reaction at temperature $T_{exo}$, wherein $T_{endo}$ and $T_{exo}$ differ from each other. The at least one reacting material is provided in at least one encapsulation within each of the chemical reaction zones
(Continued)

Figure 1:
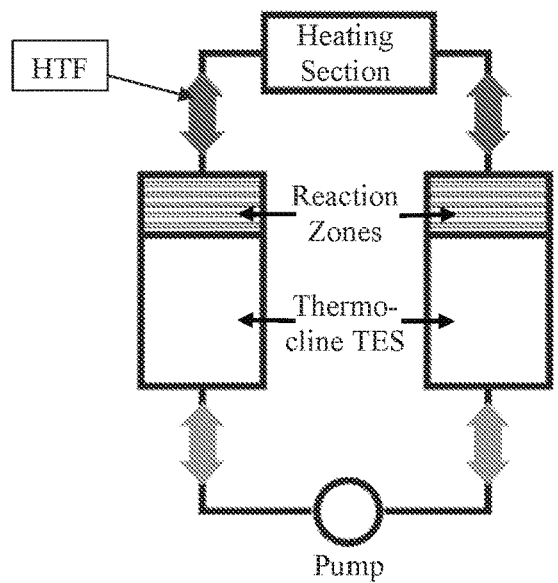

such that a contact of the reacting material and the at least one heat transfer fluid is avoided.

38 Claims, 13 Drawing Sheets

(51) Int. Cl.
*B01J 8/06* (2006.01)
*B01J 19/00* (2006.01)
*B01J 19/24* (2006.01)
*C01B 3/06* (2006.01)
*C01B 3/34* (2006.01)
*C07C 1/02* (2006.01)

(52) U.S. Cl.
CPC ............... *C01B 3/34* (2013.01); *C07C 1/02* (2013.01); *B01J 2219/00117* (2013.01); *B01J 2219/2453* (2013.01); *B01J 2219/2462* (2013.01); *B01J 2219/2465* (2013.01)

(58) Field of Classification Search
CPC ...... B01J 19/0013; B01J 19/24; B01J 19/248; B01J 19/249; B01J 2208/00; B01J 2208/00008; B01J 2208/00017; B01J 2208/00106; B01J 2208/00309; B01J 2219/00; B01J 2219/00049; B01J 2219/00051; B01J 2219/00074; B01J 2219/00117; B01J 2219/24; B01J 2219/2401; B01J 2219/245; B01J 2219/2453; B01J 2219/2461; B01J 2219/2462; B01J 2219/2465; B01J 2219/2466; B01J 2219/2469; B01J 2219/2472; B01J 2219/2476; B01J 2219/2477; B01J 2219/2482; B22F 9/00; B22F 9/16; B22F 9/30; C01B 3/00; C01B 3/02; C01B 3/06; C01B 3/061; C01B 3/063; C01B 3/34; C07C 1/00; C07C 1/02

See application file for complete search history.

(56) References Cited

U.S. PATENT DOCUMENTS

2014/0219895 A1    8/2014   Moghtaderi et al.
2014/0377158 A1   12/2014   Andrus, Jr. et al.

OTHER PUBLICATIONS

Thomasson, Phillippe, International Search Report for PCT/EP2017/075804, dated Nov. 11, 2017 [2 pages].

Jan Felinks et al.; "Particle-particle heat transfer coefficient in a binary packed bed of alumina and zirconia-ceria particles"; Applied Thermal Engineering; vol. 101; 2016; pp. 101-111.

Ivan Ermanoski et al.; "A New Reactor Concept for Efficient Solar-Thermochemical Fuel Production"; Journal of Solar Energy Engineering; vol. 135; Aug. 2013; pp. 031002-1-031002-10.

Justin Lapp et al.; "Heat Transfer Analysis of a Solid-Solid Heat Recuperation System for Solar-Driven Nonstoichiometric Redox Cycles"; Journal of Solar Energy Engineering; vol. 135; Aug. 2013; pp. 031004-1-031004-11.

Richard B. Diver et al.; "Testing of a CR5 Solar Thermochemical Heat Engine Prototype"; Proceedings of the ASME 2010 4th International Conference on Energy Sustainability; May 17-22, 2010; pp. 1-8.

Jonathan R. Scheffe et al., "Thermodynamic Analysis of Cerium-Based Oxides for Solar Thermochemical Fuel Production"; Energy and Fuels; vol. 26; 2012; pp. 1928-1936.

\* cited by examiner

THERMOCHEMICAL REACTOR SYSTEM FOR A TEMPERATURE SWING CYCLIC PROCESS WITH INTEGRATED HEAT RECOVERY AND A METHOD FOR OPERATING THE SAME

This application is a national stage application claiming priority to PCT/EP2017/075804, now WO2018073049, filed on Oct. 10, 2017, which claims priority to European Patent Application Serial No. EP16194074.7, filed on Oct. 17, 2016.

The present invention relates to a thermochemical reactor system and a method for operating the same.

Technical processes that proceed at different temperature levels are very common. Thereby one process step takes place at a higher temperature and another process step takes place at a lower temperature. The majority of these processes relates to chemical reactions requiring a catalytic or reacting material.

These processes may also be described as temperature swing cyclic processes as a multi-step process involving reversible endothermic/exothermic reactions that proceed at different temperatures.

This process category comprises reduction-oxidation processes in the area of alternative fuel production (syngas and hydrocarbon production) and oxygen separation or also adsorption-desorption processes for separating carbon dioxide and water from air and carbonation-decarbonation processes for separating carbon dioxide from air or other gases.

Syngas and Hydrocarbon Synthesis from Water and Carbon Dioxide

Alternative fuel production from renewable energies is becoming more and more important. Two widely available and abundant renewable sources are water $H_2O$ and carbon dioxide $CO_2$. Both gases can be converted to carbon monoxide CO and hydrogen $H_2$ (also known as syngas) and hydrocarbons such as methane $CH_4$ that in turn can be used for the synthesis of other valuable chemicals.

The use of solar energy as an energy source for the conversion of $H_2O$ and $CO_2$ is applicable and ecological. Thus, solar thermochemical processes for producing liquid fuels from renewable energy, $H_2O$ and $CO_2$ have been developed in the past. This conversion of intermittent solar energy into chemical fuel offers long-term storage and long-range transport of solar energy.

The solar thermochemical path is most commonly based on a two-step reduction-oxidation (redox) cycle using a metal oxide as an intermediate. In the endothermic reduction step, the metal oxide is reduced at temperature $T_{red}$ using concentrated solar radiation as the source of high-temperature process heat:

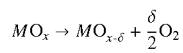

where δ is the oxygen nonstoichiometry. In the exothermic oxidation step, the metal oxide is oxidized at a temperature $T_{ox} \leq T_{red}$ with $H_2O$ and $CO_2$ to produce syngas—a mixture of $H_2$ and CO:

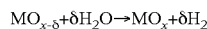

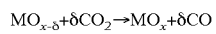

The syngas can be converted to liquid and gaseous fuels, e.g. diesel, kerosene, gasoline, methanol, and methane, and others hydrocarbon fuels, using e.g. the well-established Fischer-Tropsch synthesis and other gas-to-liquid processes. Ceria is currently considered to be the benchmark redox material for solar-thermochemical fuel production because of its morphological stability and its rapid kinetics. Typically for ceria, $T_{red} \sim 1500°$ C. and $T_{ox} \sim 800°$ C.

The most important indicator of the technical and economic feasibility of the process is the solar-to-fuel energy conversion efficiency of the two-step redox cycle, defined as:

$$\eta_{solar-to-fuel} = \frac{HHV_{H_2} n_{H_2} + HHV_{CO} n_{CO}}{Q_{solar} + Q_{penalties}}$$

where HHV is the higher heating value of the product gas, n is the number of moles produced, $Q_{solar}$ is the solar energy input and $Q_{penalties}$ is any additional energy required, such as for pumping work and gas separation.

To assess the potential efficiencies of the process, thermodynamic analyses can be applied. The maximum theoretical efficiencies of pure ceria at δ=0.1 for 0%, 50%, and 100% heat recovery, are 20%, 30%, and 60%, respectively. It is conceptually interesting to decouple reaction enthalpies from recyclable heat to understand what the ultimate thermodynamic limits of the process are. The comparison of pure pressure swing (isothermal) cycles with combined pressure-temperature swing cycles showed that maximum efficiencies are limited considerably with the isothermal cycle, irrespective of the redox material. This is due to thermodynamically limited product-gas concentrations during oxidation.

Cycles with combined pressure-temperature swings have been demonstrated in experiments and observed to lead to the highest efficiencies: the maximum demonstrated efficiency was obtained with a laboratory-scale 4 $kW_{th}$ solar reactor using ceria as redox material leading to $\eta_{solar-to-fuel} > 5\%$. In these solar experimental runs, $T_{red} \sim 1500°$ C. and $T_{ox} \sim 800°$ C., and the total pressure during reduction was $p_{tot} = 10$ mbar.

For the fuel production to be economically viable, higher efficiencies are necessary. The main improvements required to reach higher efficiencies with the solar reactor design were identified to be (Marxer et al., Energy & Fuels, Vol 29, pp. 3241-3250, 2015):

- Recuperation of sensible heat of the redox material between reduction and oxidation temperatures;
- Recuperation of sensible heat carried by the hot gases exiting the reactor;
- Reduction of reradiation losses through the reactor's aperture;
- Reduction of conduction heat losses through the reactor's thermal insulation.

Conduction losses through the insulation generally decrease with increasing reactor size as the area-to-volume ratio decreases, and are therefore less important for pilot- and industrial-scale reactors. Re-radiation losses can to some extent be diminished by higher solar concentration ratios or lower operation temperatures, where the former depends mainly on the solar optical design and the latter depends mainly on the reaction properties of the redox material.

On the other hand, sensible-heat recuperation is a matter of reactor design. It is the most crucial improvement because the energy needed to heat up the redox material from $T_{red}$ to $T_{ox}$ is typically significantly larger than the energy needed for the reaction as well as the energy lost due to re-radiation.

As aforementioned, increasing the sensible-heat recuperation from 0% to 100% leads to an increase of the maximum solar-to-fuel efficiency using ceria as redox material from 20% to almost 60% (Scheffe and Steinfeld, Energy & Fuels, vol. 26, pp. 1928-1936, 2012).

Several reactor concepts incorporating sensible-heat recuperation of the redox material have been proposed:
1. A design consisting of counter-rotating redox material rings was proposed, where one side is exposed to concentrated solar radiation and held at reduction temperature while the other side is held at oxidation temperature (Diver et al., Proceedings of ASME 4th International Conference on Energy Sustainability, Vol. 2, pp. 97-104, 2010). The counter-rotating rings act as solid-solid heat recuperators.
2. A concept with two concentric counter-rotating cylinders was developed where the hollow outer cylinder is made from ceria and the inner cylinder is made from an inert ceramic to provide a heat-recuperation mechanism (Lapp et al., Journal of Solar Energy Engineering-Transactions of the ASME, vol. 135, no. 3, 2013).
3. The approach proposed by (Ermanoski et al., Journal of Solar Energy Engineering-Transactions of the Asme, Vol. 135, no. 3, 2013) is based on a continuously moving packed bed of redox material particles. Using a solid-solid heat exchanger, the sensible energy is exchanged between the oxidized and reduced particles.
4. The concept suggested by (Felinks et al., Applied Thermal Engineering, Vol. 73, pp. 1006-1013, 2014) is also based on redox material particles. Instead of a solid-solid heat exchanger, however, a solid-phase heat-transfer medium consisting of small particles is mixed with the redox material and used to recover the sensible energy.

Syngas and Hydrocarbon Synthesis from Water and Carbon Dioxide Using Methane as Reducing Agent Alternatively, the two-step reduction-oxidation (redox) cycle using a metal oxide as intermediate can be performed using a reducing agent, such as $CH_4$, during the high-temperature reduction step to lower the required temperatures for achieving a certain reduction extend. Thereby syngas with a $H_2$ to CO ratio of 2 is produced according to:

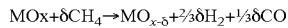

$$MOx + \delta CH_4 \rightarrow MO_{x-\delta} + \tfrac{2}{3}\delta H_2 + \tfrac{1}{3}\delta CO$$

where $\delta$ is the oxygen non-stoichiometry. The re-oxidation of the reduced metal oxide proceeds again with $H_2O$ and $CO_2$ to produce syngas:

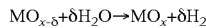

$$MO_{x-\delta} + \delta H_2O \rightarrow MO_x + \delta H_2$$

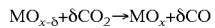

$$MO_{x-\delta} + \delta CO_2 \rightarrow MO_x + \delta CO$$

The usage of reducing agents such as methane during the reduction reaction lowers the required reduction temperature to reach similar reduction extends compared to the reduction without reducing agent. The products of the reduction with methane is a ⅓ carbon monoxide and ⅔ hydrogen syngas mixture. Subsequently, the reduced reacting material is reoxidized to its initial state with water and/or carbon dioxide to produce hydrogen and/or carbon monoxide.

Oxygen Separation from Air and Other Gas Mixtures

Renewable chemical fuels can be synthesized via solar-driven electro-, photo-, and thermochemical splitting of $CO_2$ and $H_2O$. The latter approach utilizes the entire spectrum of concentrated solar radiation as high-temperature process heat for the production of CO and $H_2$ (syngas) via metal oxide redox cycles. A critical drawback of this approach is the inert gas consumed to lower the partial pressure of oxygen ($pO_2$) for shifting the thermodynamic equilibrium of the reduction step to lower temperatures. This, in turn, requires separation of $O_2$ from the offgas for recycling the inert carrier gas and closing the material cycle.

The separation of oxygen has been a requirement in a variety of commercial applications such as oxy-combustion, autothermal gasification of carbonaceous feedstock, and for $O_2$ removal to avoid catalyst passivation by $O_2$ in fuel cells and when deoxygenating biofuels to make these more akin to petroleum-derived fuels.

Industrially, $O_2$ can be separated from air by pressure swing adsorption (PSA) with zeolites and carbon molecular sieves, by ceramic ionic-electronic conducting (MIEC) membranes, and by cryogenic distillation. PSA and MIEC membranes cannot produce high-purity inert gas and separating $O_2$ from gas mixtures at low $pO_2$ with membranes relies on a stripping gas with even lower $pO_2$. These separation technologies further require an input of electrical work ranging from 100 to 350 kWh per metric ton $O_2$, which penalizes the solar-to-fuel energy conversion efficiencies. Since solar thermochemical cycles inherently suffer from heat losses, it would be beneficial to utilize an oxygen separation technology driven by waste heat.

Thermochemical solid-state $O_2$ separation (TSSOS) with metal oxide redox materials such as $Cu_2O/CuO$, $Mn_3O_4/Mn_2O_3$, and $CoO/Co_3O_4$ utilizes low-grade process heat and does not require electricity. TSSOS has the potential to separate and concentrate $O_2$ at low $pO_2$ via temperature-swing.

The current state-of-the-art TSSOS redox material, $Cu_2O$, has a maximum oxygen exchange capacity ($\Delta\delta$, i.e., the difference in the oxygen non-stoichiometry between reducing and oxidizing conditions) of about 200 mmol $O_2$ per mol $Cu_2O$, exchanged at approximately 10 µmol $O_2$ min$^{-1}$ g$^{-1}$ $Cu_2O$ when cycled between 1120 and 1450 K. However, $Cu_2O$ cannot be employed with low-grade process heat at 600-900 K.

Perovskites offer an alternative material that is able to utilize low-grade solar thermal energy at lower temperatures, such as waste heat from solar fuel production processes. Perovskites offer high oxygen conductivity and a stable crystal structure over a large range of oxygen non-stoichiometry.

The oxygen exchange capacity characterizes the trade-off between high energy conversion efficiencies at low temperature during the endothermic reduction and high rates and extends of the oxygen separation process at high oxide reduction temperatures. For a perovskite with $ABO_{3-\delta}$ stoichiometry—where A and B are metal cations in twelve- and six-coordinated interstices—the TSSOS redox cycle can be represented with:

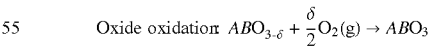

$$\text{Oxide oxidation: } ABO_{3-\delta} + \frac{\delta}{2}O_2(g) \rightarrow ABO_3$$

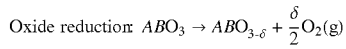

$$\text{Oxide reduction: } ABO_3 \rightarrow ABO_{3-\delta} + \frac{\delta}{2}O_2(g)$$

Conceptually, $O_2$ is stripped from a gas mixture at low $pO_2$ via oxidation of the perovskite at low temperatures. This yields as an output of the oxidation step an inert gas with a lowered $pO_2$, while concentrated $O_2$ is evolved from the solid at an elevated temperature and increased $pO_2$ via partial reduction of the metal oxide. Thermogravimetric analysis and high-temperature X-ray diffraction for $SrCoO_{3-\delta}$, $BaCoO_{3-\delta}$ and $BaMnO_{3-\delta}$ perovskites and $Ag_2O$ and $Cu_2O$ references show the superior performance of $SrCoO_{3-\delta}$, surpassing with an oxygen exchange capacity of 44 mmol $O_2$ $mol^{-1}$ $SrCoO_{3-\delta}$ exchanged at 12.1 μmol $O_2$ $min^{-1}$ $g^{-1}$ at 600-900 K the performance of state-of-the-art $Cu_2O$ at these conditions.

Adsorption/Desorption of Carbon Dioxide and Water from Air and Other Gas Mixtures Among several strategies to mitigate anthropogenic $CO_2$ emissions, capturing $CO_2$ directly from ambient air—usually referred to as direct air capture (DAC)—has recently attracted increasing interest. The advantage of DAC is its ability to address present and past emissions from distributed and mobile sources, e.g., derived from the transportation sector. Furthermore, DAC systems need not be attached to the source of emission but can be logistically centralized and located next to the site of $CO_2$ storage/processing or of vast renewable (e.g. solar) energy resources. In particular, $CO_2$ extracted from the atmosphere can be processed to synthetic liquid hydrocarbon fuels using renewable energy in a closed material cycle. Thereby, DAC uniquely offers the possibility of a truly sustainable liquid fuel-based energy future. While some studies claim that DAC can potentially become competitive and others question its economic feasibility, it is evident that additional R&D on the fundamentals of DAC is required to reliably assess its ultimate industrial-scale applicability.

If, additionally, $H_2O$ is co-extracted from ambient air, major logistical benefits can be achieved in the production of synthetic liquid hydrocarbon fuels using concentrated solar energy. Solar fuel production plants will be located in deserted regions of the earth's sunbelt with vast direct solar irradiation but limited or no fresh water resources. Water co-extracted in a DAC process can thus become a valuable by-product. Note that, if seawater is accessible, fresh water extraction via reverse osmosis desalination is about two orders of magnitude more energy efficient than water extraction from air via adsorption.

Solid amine-functionalized materials have been identified as promising sorbents for DAC, as they offer relatively high specific $CO_2$ capacities and uptake rates under extremely low $CO_2$ partial pressures, such as in the case of ambient air. The vast majority of previous studies on these materials focused on maximizing their $CO_2$ adsorption capacity, while sorbent regeneration was usually achieved by purging with an inert gas, yielding—again—highly diluted $CO_2$. Desorption of concentrated, high-purity $CO_2$ is evidently crucial for downstream applications, yet this issue remained mostly disregarded. A few studies applied steam stripping, moisture swing, or temperature-vacuum swing (TVS) processes to obtain concentrated $CO_2$ from the air.

Another intriguing advantage of amine-functionalized solid sorbents is their tolerance to air moisture. In contrast to physical sorbents such as zeolites, an increase of the $CO_2$ adsorption capacity was observed under humid conditions compared to dry conditions. However, substantial amounts of water are co-adsorbed from moist gases. Formation of carbamates and carbamic acid was postulated as the main underlying $CO_2$ adsorption mechanism on amine-modified silica under dry and humid conditions. Similar mechanisms were concluded for amine-modified cellulose. Additional adsorption of $H_2O$ presumably occurs through physical adsorption.

As opposed to flue gases, the molar water content of air is typically one to two orders of magnitude higher than its $CO_2$ content. Thus, water adsorption per gram of sorbent material can substantially exceed $CO_2$ adsorption. This in turn implies significant heat requirements for water desorption during sorbent regeneration. The required heat of water desorption will typically be of the same order of magnitude as the heat of evaporation of the co-adsorbed water. Although several proposed DAC concepts are based on amine-functionalized materials, their co-adsorption of water during $CO_2$ capture has hardly been quantified. Data on $H_2O$ adsorption on an amine-based sorbent was shown for spacecraft air regeneration without $CO_2$ concentration. Water adsorption isotherms on amine-grafted pore expanded mesoporous silica gel were measured but only for single component adsorption. Co-adsorption of $CO_2$ and $H_2O$ on amine-functionalized silica was analyzed in column-breakthrough experiments but no concentrated $CO_2$ was extracted.

The specific energy requirements of the TVS process based on the measured $H_2O$ and $CO_2$ capacities are estimated to be 12.5 kJ/$mol_{CO2}$ of mechanical (pumping) work and between 493 and 640 kJ/$mol_{CO2}$ of heat at below 100° C., depending on the air relative humidity. For a targeted $CO_2$ capacity of 2 mmol/g, the heat requirement would be reduced to between 272 and 530 kJ/$mol_{CO2}$, depending strongly on the amount of co-adsorbed water.

$CO_2$ Capture from Air Via a Carbonation-Decarbonation Thermochemical Cycle

Most $CO_2$ capture technologies deal with the decarbonization of fossil fuels prior to combustion or with the separation of $CO_2$ from combustion flue gases. $CO_2$ capture from ambient air could become necessary for achieving stabilization of the global $CO_2$ concentration in the atmosphere in view of increasing emissions derived from transportation and other distributed sources.

The capture of $CO_2$ from air—vis-à-vis capture from a flue gas stream—is thermodynamically unfavorable because of the higher Gibbs free energy change needed to separate a much more diluted gas. However, in this case, the capture plant could be strategically located next to a source of renewable energy and to the final storage site, such as inhabited deserts with high solar irradiation and vast geological storage reservoirs. There are logistical and environmental advantages for capturing $CO_2$ from the air, taking place far away from populated cities and without generating additional $CO_2$ for its capture and transportation.

Of special interest is the carbonation-calcination thermochemical cycles based on CaO, represented by the net reversible reaction:

$$CaO+CO_2=CaCO_3 \; \Delta H°_{298K}=-178 \text{ kJ mol}^{-1}$$

This reaction has been extensively study for separating $CO_2$ from combustion flue gases, and is presently being considered for separating $CO_2$ from air using solar energy.

As mentioned above all these processes have in common that they require a temperature swing involving reversible endothermic/exothermic reactions that proceed at different temperatures.

Thus, it is desirable to provide a reactor system for such temperature swing processes that can be operated at different temperatures. It would be in particular desirable to provide a concept for temperature swing cyclic processes wherein thermal energy released in one process step can be stored and recycled into the thermochemical cycle for processes requiring thermal energy.

The object of the present invention is thus to provide such a reactor system with reaction zones operating at different temperatures such that yield and overall efficiency of the process is increased.

This object is being solved by a thermochemical reactor system and a method for operating the same.

Accordingly, a thermochemical reactor system for a temperature swing cyclic process with integrated heat recovery is provided that comprises
- at least two modules, wherein each module comprises at least one chemical reaction zone (CRZ) and at least one thermal energy storage unit (TES),
- wherein the at least two modules are operationally connected for at least one heat transfer fluid (HTF) for transporting heat between the two modules,
- wherein each chemical reaction zone (CRZ) comprises at least one reacting material that undergoes in a reversible manner an endothermic reaction at temperature $T_{endo}$ and an exothermic reaction at temperature $T_{exo}$, wherein $T_{endo}$ and $T_{exo}$ differ from each other,
- wherein the at least one reacting material is provided in at least one encapsulation within each of the chemical reaction zones (CRZ) such that a contact of the reacting material and the at least one heat transfer fluid is avoided.

It is also possible to describe the encapsulation (or encasement) as a separate reaction chamber for the reacting material. The arrangement of the reacting material in an encapsulation or reaction chamber allows for a separation of the reacting material from the heat transfer fluid transporting the heat in and out of the reacting material in the respective reaction zone has several advantages:
- The HTF does not need to be inert with the reacting material, such as a redox material, and can be e.g. air.
- The HTF is not contaminated during the temperature cycle (e.g. redox cycle) with $O_2$ and $O_2$ can be separated as a byproduct.
- The thermal storages and the reaction zones can be operated at different pressures and gas atmospheres. For example, the thermal storage units can be operated at $P>P_{ambient}$ (overpressure) to decrease the pumping work, while the reaction zone can be operated at $P<P_{ambient}$ (vacuum) to enhance the chemical reaction.
- The products from the 2-step thermochemical cycle can be extracted easily since they are produced within the encapsulation in a relatively small volume (compared to the storage volume).

If the reacting material is not encapsulated and thus not separated from the HTF, the HTF must be inert and cannot contain $O_2$ as this would prohibit the chemical reactions. In this case, inert HTFs, such as Ar or $N_2$ need to be used which are contaminated by the produced $O_2$ during thermochemical cycling and therefore need to be cleaned by a separate process to be reused again. This induces both energy and economical penalties.

In one embodiment of the present reactor system the at least one reacting material in each chemical reaction zone is at least one metal oxide undergoing reduction at reduction temperature $T_{red}$ and oxidation at oxidation temperature $T_{ox}$, wherein $T_{red}$ and $T_{ox}$ differ from each other. In particular, $T_{red}>T_{ox}$.

A metal oxide may be used in
a) the reduction-oxidation of a reacting material for the conversion of water and carbon dioxide to syngas comprising hydrogen and carbon monoxide;
b) the reduction-oxidation of a reacting material for the conversion of water and carbon dioxide to hydrocarbons, in particular $CH_4$;
c) the reduction of a reacting material by the aid of a reducing agent such as methane to obtain the reduced reacting material and synthesis gas. Subsequently, the reduced reacting material is oxidized with water and/or carbon dioxide to form the initial reacting material and hydrogen and/or carbon monoxide, and/or
d) the reduction-oxidation of a reacting material for the separation of oxygen from air or from any other gas mixtures.

The metal oxide used in a), b), and c) may comprise $CeO_2$, $CeO_2$ doped with at least one transition metal, and/or at least one rare earth metal oxide or at least one perovskite.

Dopants considered for ceria-based cycles include +2 (Ca, Sr, Li), +3 (Sm, Gd, Y, Cr, Pr, La, Sc) and +4 (Zr, Hf) cations. By changing the thermodynamic and kinetic properties of ceria by doping its fluorite structure with transition metal and rare earth metal oxides the reduction and oxidation temperatures can be influenced, such that the material can be reduced at a lower $T_{red}$. This typically goes hand in hand with a lower $T_{ox}$ which is required to fully oxidize the material back to its initial state.

Perovskites of the generic form $ABO_3$ are a further alternative redox material. Similar to doping $CeO_2$, perovskites such as $La_{1-x}Sr_xMnO_3$ (x=0.3-0.4) show different thermodynamic and kinetic properties compared to pure ceria and thus allow operating at lower $T_{red}$ and $T_{ox}$.

The metal oxides in d) may comprise $Cu_2O/CuO$, $Mn_3O_4/Mn_2O_3$, and $CoO/Co_3O_4$ or perovskites like $SrCoO_{3-\delta}$, $BaCoO_{3-\delta}$ and $BaMnO_{3-\delta}$.

In another embodiment of the present reactor system the at least one reacting material in each chemical reaction zone is at least one material undergoing adsorption at adsorption temperature $T_{adsorp}$ and desorption at desorption temperature $T_{desorb}$ of at least one compound, in particular at least one gas, wherein $T_{adsorp}$ and $T_{desorb}$ differ from each other.

This is for example applicable in case of adsorption-desorption by a reacting material for the separation of carbon dioxide and/or water from air or from any other gas mixtures containing any of these compounds. Here the reacting material may be a solid amine functionalized material, for example, N-(2-aminoethyl)-3-aminopropylmethyl-dimethoxysilane and fibrillated cellulose suspension.

In a further embodiment of the present reactor system the at least one reacting material in each chemical reaction zone is at least one material that undergoes a carbonation reaction at temperature $T_{carb}$ and a decarbonation at temperature $T_{decarb}$ with $CO_2$, wherein $T_{carb}$ and $T_{decarb}$ differ from each other.

This is for example applicable in case of the carbonation/decarbonation of a reacting material for the separation of $CO_2$ from ambient air or from any other gas mixture. Here the reacting material may be an alkali oxide or earth alkali oxide, in particular CaO that is converted to $CaCO_3$ during carbonation.

In a preferred embodiment of the present reactor system each of the two chemical reaction zones is adjacent to the corresponding thermal energy storage unit; i.e. the first chemical reaction zone is adjacent to the first thermal energy storage unit and the second chemical reaction zone is adjacent to the second thermal energy storage unit. In this context "adjacent" means in direct contact to each other, for example the chemical reaction zone is arranged on top of the thermal storage unit.

Thus, it is in particular preferred if each of the two chemical reaction zones is arranged on top of the corresponding vertically oriented thermal storage units. Said vertical arrangement of the thermal storage unit allow for exploiting stratification and to ensure a radially well-distributed particle bed. Thus, a dual-storage reactor system is provided that consists of two vertically oriented thermal storage units such as packed beds of inert material on top of which the chemical reaction zone comprising the encapsulated reacting material is placed.

In another preferred embodiment of the present reactor system the at least one encapsulation containing the reacting material is arranged perpendicular, parallel or in any other angle to the flow direction of the heat transfer fluid through the chemical reaction zone.

In a variant of the present reactor system the reacting material is provided in at least two encapsulations, preferably three, four or more in each of the chemical reaction zones.

In a yet further embodiment the at least one encapsulation is provided in form of at least one tube or a chamber.

The tubes or chambers allow preferably for a parallel and/or perpendicular arrangement of the encapsulated material to each other.

In case the reacting material is provided in tubes, the tubes may be arranged parallel to each other in a single layer or in multiple layers. The multiple layers may be further stacked parallel or perpendicular to each other. It is also possible that the tube layers are offset to each other and are arranged in any suitable angle between 1-90°; i.e. the tube layers may be rotated about any suitable angle such as 90°.

In case the reacting material is provided in a chamber, such chamber may be inserted into an encasement. The chamber may be formed like a groove engraved into a material block. There may be several of such grooves arranged parallel to each other in the material block. The chambers or grooves are preferably arranged perpendicular or in any suitable angle between 1-90° to the HTF flow direction. In a particular preferred embodiment the reacting material can be encapsulated in stacks similar to fuel-cell stacks. Thereby, the heat transfer fluid flows through dedicated channels while the reacting material is contained in separated chambers.

In yet a most preferred embodiment of the present reactor system the at least one encapsulation is provided as a tube with at least one gas inlet (for instance for feeding $CO_2$ and $H_2O$ into the redox material having temperature $T_{ox}$) and at least one gas outlet (for instance for transporting syngas obtained after oxidation out of the redox material having temperature $T_{ox}$).

The encasement or encapsulation may be made of any thermally conductive material, in particular aluminium oxide or silicium carbide or high temperature alloys.

In general the encasement or encapsulation material should have the following properties:
- It should be inert with both the storage material and the reacting material, such as redox material;
- It has to withstand the required temperatures ($T_{max} \geq T_{red}$);
- It should offer a good heat transfer from the HTF to the reacting material, should thus have a high thermal conductivity; and
- It should suppress the diffusion of $O_2$ from the HTF to the reacting material, such as redox material.

Aluminium oxide $Al_2O_3$ can be used for instance in case $CeO_2$ and related doped $CeO_2$ or perovskites are used as redox material. A potential alternative could be silicium carbide SiC. In case the reactor is operated at $T_{max} < 1200°$ C. for example by using a new perovskite redox material (which allows operation at these temperature) or by using reducing agents such as $CH_4(g)$, $H_2(g)$ or $C(s)$, which promote the reduction of the redox material, then also high temperature alloys such Inconel may be used as encapsulation material.

In yet a further preferred variant of the present reactor system at least two, preferably at least three reacting materials with different reduction/oxidation temperatures or different adsorption/desorption temperatures are used, wherein the different reacting materials are arranged in series along the flow direction of the HTF. The reacting materials (e.g. redox material) may be arranged such that $T_{red/ox\_Material\ 1} > T_{red/ox\ Material\ 2} > T_{red/ox\ Material\ 3}$. Said arrangement may also be described as a cascaded redox reactor.

In this case each of the reacting materials may be arranged in a tube or stack such that a temperature gradient is created between the reacting materials, wherein the tubes and stacks are preferably arranged perpendicular to the HTF flow direction.

The reacting materials are encapsulated in tubes or stacks to prevent direct contact of the heat transfer fluid and the reacting materials. Thereby, the different reacting materials are arranged along the height of the reactive zone, such that the different thermodynamic and kinetic properties of the individual materials, e.g. reduction and oxidation behavior, fit best the temperature distribution inside the chemical reaction zone. For example, in the top part of the chemical reaction zone where the highest temperatures are reached, a material with suitable thermodynamic and kinetic properties for these temperatures is selected, e.g., $CeO_2$. In lower levels of the reaction zone, where the temperatures are lower than in the top part, reacting materials with different thermodynamic and kinetic properties than in the top part are selected which operate favorably at these lower temperatures, e.g. doped $CeO_2$ or perovskites.

It is also possible that the different reacting materials are encapsulated parallel to the HTF flow direction. In this case, the different reacting materials can be layered within the same encapsulation such that again the material with the most appropriate thermodynamic and kinetic properties at the highest temperature is positioned in the hottest region while the one with the most appropriate thermodynamic and kinetic properties at lower temperatures is positioned in the region of the reactive zone where the lowest temperatures are obtained.

In any case the inlet of reactants is at the CRZ that contains the reacting material with the least favorable reaction thermodynamics and kinetics for the oxidation with $H_2O$ and/or $CO_2$ and that the product gas of a CRZ is the reactant gas of a CRZ that contains the reacting material with the next favorable thermodynamics and kinetic properties for the oxidation with $H_2O$ and/or $CO_2$.

The thermal energy storage units may store thermal energy in form of sensible heat (SHS) and/or latent heat (LHS), and/or heat of reaction of reversible thermochemical processes (TCS).

SHS systems achieve storage by raising the temperature of a storage material, usually a solid or liquid. The storage of sensible heat in such a material depends strongly on its heat capacity, which determines the energy density and the thermal diffusivity. Potential solid SHS materials are for instance rock, concrete, ceramics, sand, or metals. The most presently used liquid SHS material comprises synthetic oils and molten salts.

In a LHS system the additional heat is stored as the enthalpy of phase transition of the storage material. Thus, these systems utilize materials that change phase at high temperatures, such in case of solid-liquid or liquid-gas transitions.

The TCS system uses the heat from a heat source such as the solar field to drive reversible chemical reactions. Hereby, the reaction in the forward direction is the endothermic reaction (taking up the heat) while the reverse reaction is exothermic (releasing heat). The amount of heat stored in a chemical reaction depends on the heat of reaction and the extent of conversion. Thus, in a TCS the heat is looped via reversible chemical reactions: It is stored as the enthalpy of the endothermic reaction and recovered as sensible heat through the exothermic recombination of the reactants.

In the present case the thermal energy storage units may comprise ceramic bricks, $ZrO_2$ pellets, silica or alumina spheres as heat storage material. Said heat storage materials used in the thermocline TES allow for storing and releasing heat as the redox material is brought to $T_{red}$ and $T_{ox}$. The storage material at the top of the TES has to withstand temperatures as high as $T_{red}$, e.g., 1500° C. when ceria is used as redox material. Such high temperatures are common in regenerators used in the steel industry, where ceramic bricks are used to preheat air up to 1300-1600° C. $ZrO_2$ pellets were tested between 25 and 980° C. Silica and alumina are also resistant to very high temperatures. To reduce the cost of the storages, different storage materials may be used along the axial direction, depending on the temperature history and the maximum thermal and mechanical stresses at a given axial position.

A packed bed of alumina spheres is proposed as preferred thermal storage unit. Alumina has a high storage density and is compatible with the elevated temperatures. A trade-off exists for the size of particles used in the storages. Small particles increase convective heat transfer rates and hence thermal stratification, however, they also increase the pressure drop. One optimization approach is to use bigger particle sizes for the storage material that is exposed to higher temperatures where the pressure drop is higher, while the material that is exposed to lower temperatures may have smaller particle sizes to increase heat transfer.

The present reactor system is furthermore coupled or connected to at least one external source of thermal energy (ESE) for heating the heat transfer fluid in a heating section that is operationally connected to the chemical reaction zones and the thermal energy storage unit. The external source of thermal energy may obtain process heat from a solar receiver and/or electrical heating elements and/or plasma torches and/or combustion of fuels. However, the use of solar energy for heating the heat transfer fluid is preferred.

The heat transfer fluid (HTF) used for transporting heat from the heating section through the chemical reaction zones and thermal storage unit may be air, carbon dioxide, helium, argon, nitrogen, steam, molten salt, molten/liquid metals, molten glass, synthetic oils.

Furthermore, the HTF of the heating section can be different from the HTF in the TES and coupled by a heat exchanger. In this case, possible HTF for the heating section comprise besides the aforementioned HTF also solid particles of silicon carbide, alumina, silica, zirconia, and other ceramics.

As previously mentioned the present reactor system is constructed such that it allows for operating the reacting material in the chemical reaction zones at different temperatures.

Thus, a method is provided for operating the reactor system, wherein one of the two chemical reaction zones is operated at the temperature $T_{endo}$ of the endothermic reaction and the other chemical reaction zone is operated at the temperature $T_{exo}$ of the exothermic reaction of the reacting material, wherein the heat required for the chemical reaction zones is provided by a heat transfer fluid.

The heat transfer fluid transports the required process heat from one module comprising the first chemical reaction zone and the first thermal storage unit to the other second module comprising the second chemical reaction zone and the second thermal storage unit. The heat transfer fluid flows thus through the first module and subsequently through the second module. The flow direction will be switched if the reactions in the endothermic zone and the exothermic zone reached a predetermined level as will be explained in more detail further below. Thus, the present method may be conducted as a cycling process; HTF is pumped back and forth between both modules.

In one embodiment of the present method one of the two chemical reaction zones is operated at the reduction temperature $T_{red}$ and the other chemical reaction zone is operated at the oxidation temperature $T_{ox}$ of a metal oxide used as reacting material. Possible metal oxides are described above.

As previously described, the metal oxide as reacting material may be used for converting water and carbon dioxide to syngas comprising hydrogen and carbon monoxide.

Yet, the metal oxide as reacting material may also be used for converting water and carbon dioxide to hydrocarbons, in particular $CH_4$.

The metal oxide as reacting material may also be used for converting methane or other gaseous hydrocarbons to hydrogen and carbon monoxide.

It is furthermore possible to use the metal oxide as reacting material for the separation of oxygen from air or from any other gas mixtures.

In another embodiment of the present method one of the two chemical reaction zones is operated at the adsorption temperature $T_{adsorp}$ and the other chemical reaction zone is operated at the desorption temperature $T_{desorb}$ of the reacting material.

In this case, the adsorbing/desorbing reacting material may be used for the separation of carbon dioxide and/or water from air or from any other gas mixtures containing any of these compounds. Suitable materials are listed above.

In yet a further embodiment of the present method one of the two chemical reaction zones is operated at the carbonation temperature $T_{carb}$ and the other chemical reaction zone is operated at the decarbonation temperature $T_{decarb}$ of the reacting material.

In this case the reacting material undergoing carbonation/decarbonation may be used for the separation of $CO_2$ from ambient air or from any other gas mixture. A preferred material is CaO.

The heat transfer fluid provides the required process heat for the chemical reaction zones. This is done by pumping the heat transfer fluid that is heated in the heating section by an external source of thermal energy through the respective chemical reaction zone.

The main challenge of sensible heat thermocline TES solutions (such as packed bed of rocks) is thermocline degradation, leading to an outlet temperature drop during discharging, an outlet temperature increase during charging, limited storage utilization factors and potentially reduced power block efficiencies. Typical reasons for thermocline degradation are: (1) limited heat transfer rates between HTF and storage material, (2) axial heat conduction and radiation along the storage, (3) heat exchange with storage container/insulation, and (4) mixing of HTF with different temperatures due to vertical flows at the inlet and outlet and bypass flows at the wall. The effect of these mechanisms can be decreased by choosing e.g. higher height-to-diameter ratios of the TES, smaller storage filler particles or lower mass flow rates. However, these design parameters are subject to disadvantages such as increased pumping work or insufficient heat rates and therefore their influence on the thermocline steepness is limited. One solution to address the temperature drop during discharging is the use of phase-change materials at the top of the storage to stabilize the outflow temperature during discharging.

An alternative approach is to actively increase and maintain the thermocline steepness inside the tank and is referred to as thermocline control. Various thermocline control concepts were proposed in the past, such as:

a) Periodically flush the TES to push the thermocline out of the storage: The drawback is that the energy extracted during the flushing is at low temperature and might be lost unless the plant has a system that can utilize this lower temperature HTF.

b) The use of a floating barrier to separate cold and hot fluid: It has the potential to strongly reduce the thermal degradation in a TES. However, this can only be applied to systems where the HTF is also the storage material and it is not compatible with the usage of filler material.

c) Addition of phase change material (PCM) to decrease the temperature drop during discharging and increase storage utilization factors: Although PCMs are typically significantly more expensive than low cost sensible storage filler material, cost reductions are possible.

d) Siphoning for thermocline re-establishment: This method consists of an additional port (distributor) inside the TES which is used to extract the thermocline while hot and cold HTF are injected at the top and at the bottom, respectively. However, the energy extracted during the siphoning process is at an intermediate temperature and it might not be possible to us it for the process at this temperature.

e) Extracting, upgrading and returning fluid at certain positions of the thermocline: Additional ports inside the TES are used to extract HTF at intermediate temperatures, upgrade it with thermal energy and return it at the top (hot side) into the TES. In a concentrated solar power plant this is particularly interesting, since this method can be applied during low solar insulation periods.

f) Sliding flow to decouple pressure drop effects from heat transfer effects: The packed bed is divided into multiple segments with a port in-between all adjacent segments. Inlet and outlet are always connected to ports such that the HTF flows through two TES segments. After the first segment is fully saturated the inlet and outlet ports are switched to the consecutive segments.

However, the approaches have several drawbacks as just described.

These drawbacks can be overcome by injecting the heat transfer fluid ahead of the thermocline. Thus, in an embodiment of the present method the temperature and temperature profile (or thermocline) of the chemical reaction zones is additionally controlled (or maintained) by extracting, heating and injecting the heated heat transfer fluid at different positions along the chemical reaction zones and/or the thermal energy storage units.

The temperature profile may be controlled by extracting or injecting the heat transfer fluid at multiple ports arranged along at least one or each of the modules of the reactor system. Several additional ports are placed inside the TES. The thermocline is then steepened by injecting fluid ahead of the thermocline front based on certain criteria as set out below.

It is furthermore preferred, if the thermocline (or temperature profile) inside at least one module or in both modules is steepened by injecting HTF at an intermediate position of the thermocline, cutting off a certain portion of the thermocline. In this case, the criteria for switching the HTF injection port may be determined based on comparing the actual stored energy between two ports and a target/reference energy.

In another variant the temperature profile may be controlled by extracting HTF at one port of a module and injecting it back at another port of a module.

In an embodiment of this method applied during the charging phase the inlet port is switched before the whole thermocline region has passed the respective port. This leads to a cut-off of the thermocline, entrapping a portion of the thermocline within the storage tank while the charging continues between the new inlet port and the outlet port with a steeper thermocline. During the following discharging, the entrapped portion of the thermocline is flattened out due to dispersion effects (axial conduction, limited convective heat transfer) and gets then pushed out of the tank. The analogous injection strategy can be performed during charging.

Finding a viable criteria for switching ports is challenging. The goal is, that the injection ports are switched such that when the flow is reversed, the outlet temperature stays in a certain temperature range $\Delta T$. There is no simple relation between the entrapped thermocline portion and the outlet temperature variation that will be caused from it during the next charge/discharge phase. The mentioned outlet temperature variation is dependent on the distance of the entrapped section to the outlet of the next phase and multiple heat transfer effects.

One possible injection port change criteria is based on the energy stored in the section of the tank between the active inlet port ($x_i$) and the location of the next port that is supposed to be used for injection ($x_{i+1}$). As soon as this energy reaches a certain reference energy, the injection port is switched. If this reference energy is defined as energy of the section at a temperature $\delta T$ below/above the charging/discharging temperature, the criteria can be written as follows:

$$\int_{x_i}^{x_{i+1}} h(T(x))dx = \int_{x_i}^{x_{i+1}} h(T_h - \delta T_h)dx \qquad (a)$$

$$\int_{x_i}^{x_{i+1}} h(T(x))dx = \int_{x_i}^{x_{i+1}} h(T_c - \delta T_c)dx \qquad (b)$$

Equations (a) and (b) correspond to the injection port change criteria for the charging and discharging phase, respectively. The choice of $\delta T$ was found to yield good results if it was set to the same value as $\Delta T$:

$$\delta T_h = \Delta T_h \qquad (c)$$

$$\delta T_c = \Delta T_c \qquad (d)$$

It is also possible to additionally control the temperature (temperature profile or thermocline) of the chemical reaction zones by flushing the thermal energy storage unit to transport the stored heat into the respective chemical reaction zone.

Another approach for additionally controlling the temperature (temperature profile or thermocline) of the chemical reaction zones is a combination of sensible heat storage (SHS), latent heat storage (LHS) and/or thermochemical heat storage (TCS).

Due to the construction features of the present reactor system (in particular due to the encapsulation of the redox material) it is also possible that the atmosphere and pressure of the chemical reaction zone and the thermal energy storage units are controlled separately.

According to the present method one of the two chemical reaction zones is operated at the endothermic temperature of the reacting material, e.g. reduction temperature of the redox material. In the course of the (endothermic) reduction of the redox material oxygen is released that needs to be flushed out or extracted.

Thus, in an embodiment of the present method the one of the two chemical reaction zones operated at the reduction temperature $T_{red}$ of the redox material is flushed with an inert gas and/or operated at vacuum pressures, such that the evolved oxygen from the redox material is removed out of the chemical reaction zone. This reaction step can be performed at ambient pressure or vacuum conditions.

Thus, in an embodiment of the present method the one of the two chemical reaction zones operated at the reduction temperature $T_{red}$ of the redox material is flushed with an inert gas and the oxygen released by the redox material is flushed out of the chemical reaction zone with the inert gas.

According to the present method the other of the two chemical reaction zones is operated at the exothermic temperature of the reacting material, such as at the oxidation temperature of a redox material. In the course of the (exothermic) oxidation for example the $CO_2/H_2O$ fed into the redox material is reduced to $CO/H_2$ while the reduced redox material is oxidized to its original state. This reaction step can be performed at ambient pressure or over-pressure.

Thus, in case of a syngas process carbon dioxide and water are fed (through one inlet) to the one of the two chemical reaction zones operated at the oxidation temperature $T_{ox}$ of the redox material, wherein carbon dioxide and water are converted to carbon monoxide and hydrogen that are subsequently discharged from the chemical reaction zone (through an outlet).

In yet another embodiment of the present method the flow direction of the heat transfer fluid transporting the heat from the heating section to the chemical reaction zones and the thermal storage units is switched if the redox material in the one of the two chemical reaction zones operated at the reduction temperature $T_{red}$ of the redox material is reduced to a certain reduction extend $\delta$, for ceria typically in the range of $\delta=0.01-0.1$ and/or if the redox material in the other chemical reaction zone operated at the oxidation temperature $T_{ox}$ of the redox material is oxidized back to a certain reduction extend.

Figure 2A:
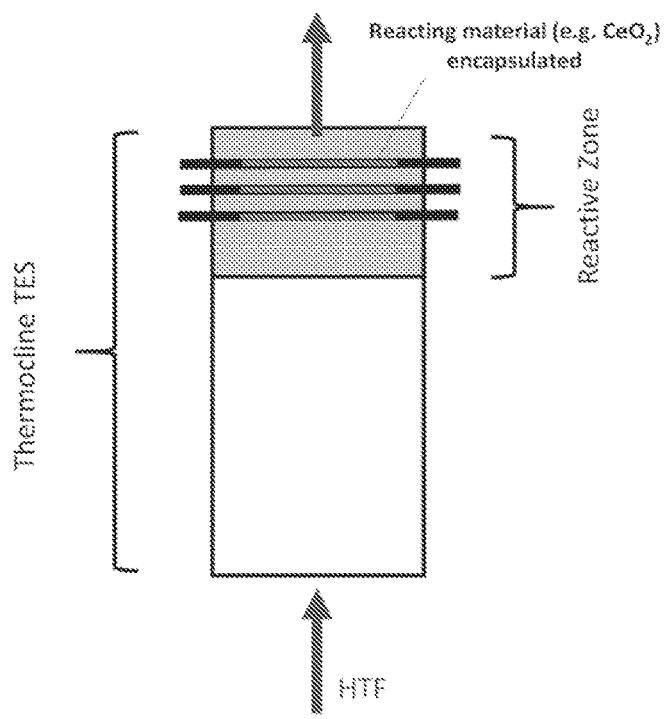
Figure 2B:
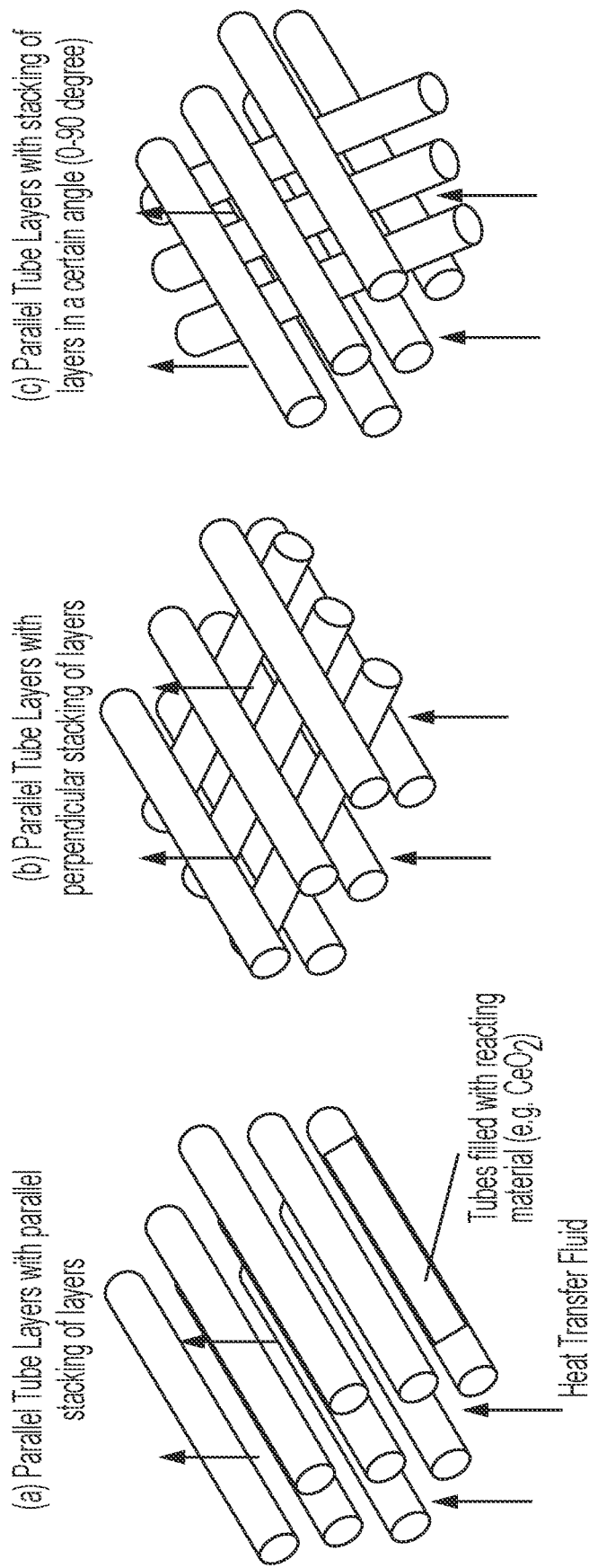
Figure 2C:
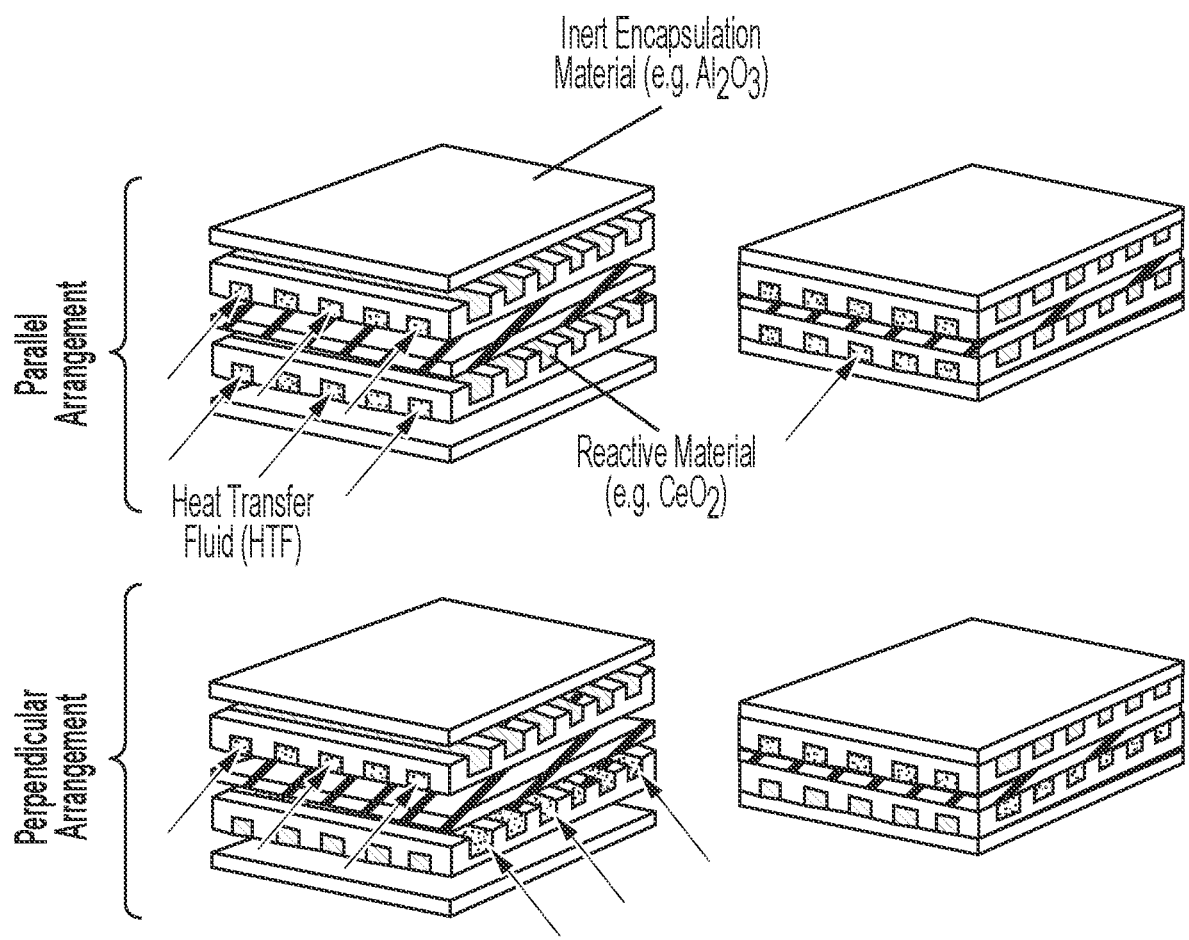
Figure 2D:
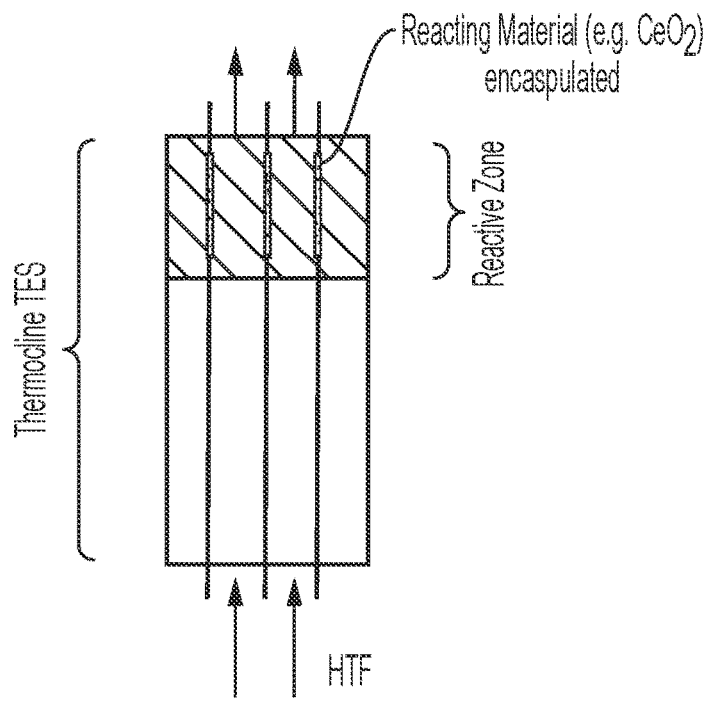
Figure 2E:
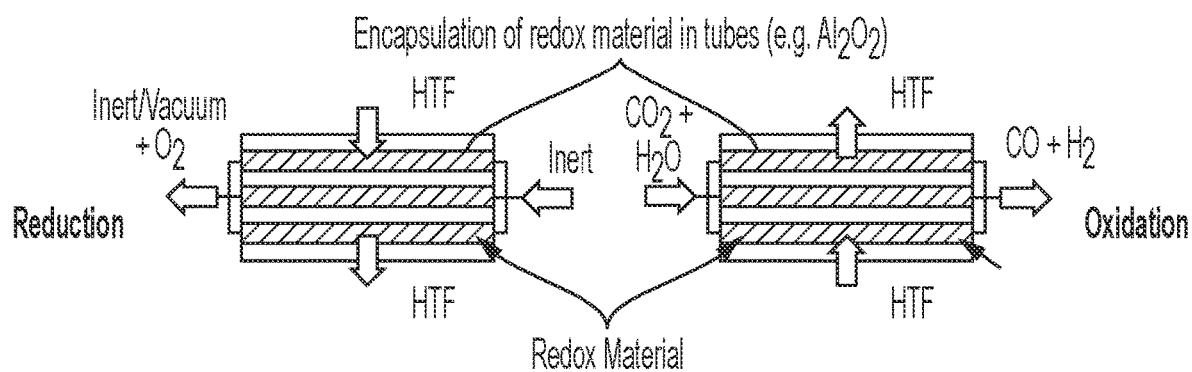
Figures 1, 3A:
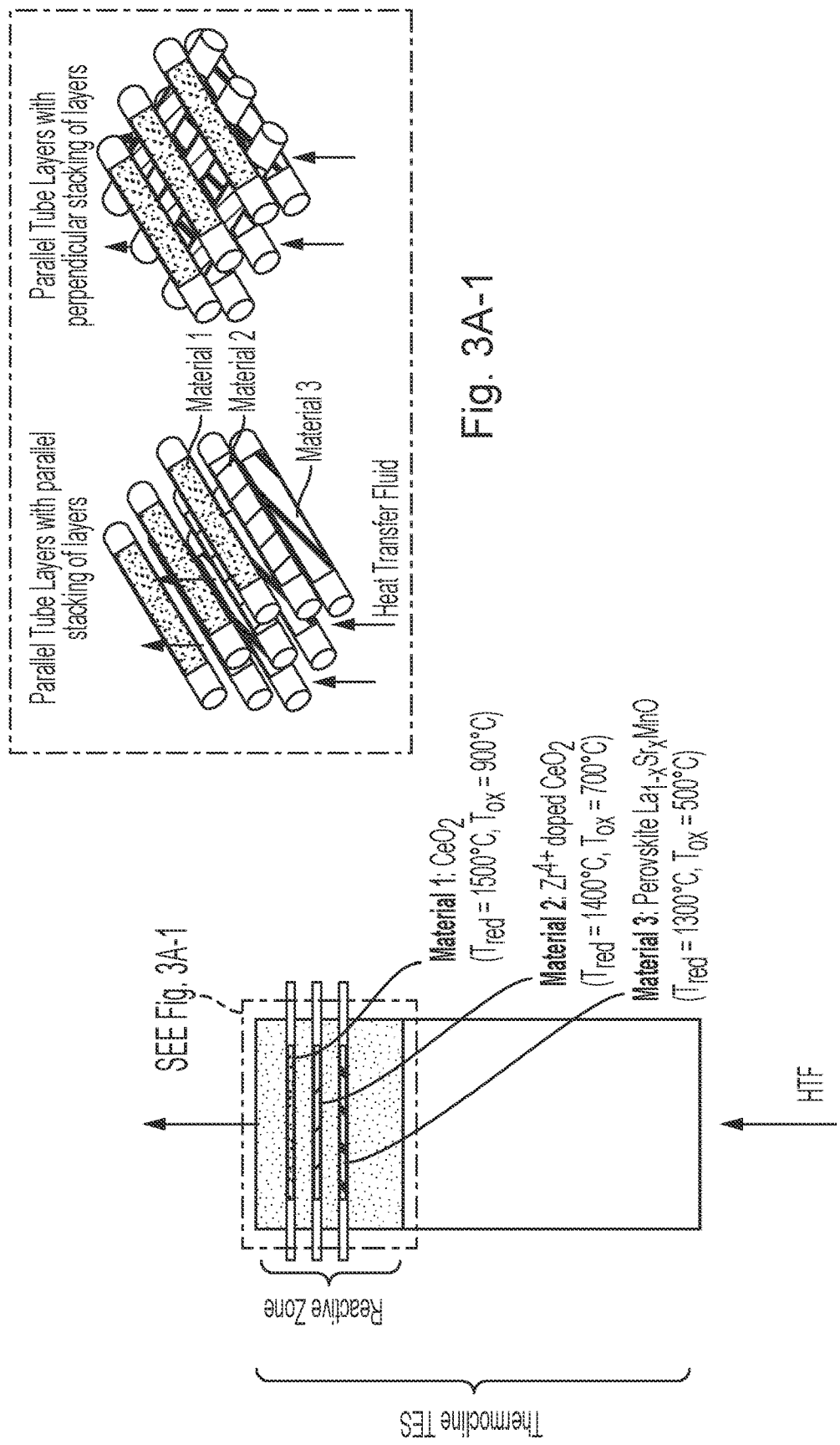
Figures 1, 3B:
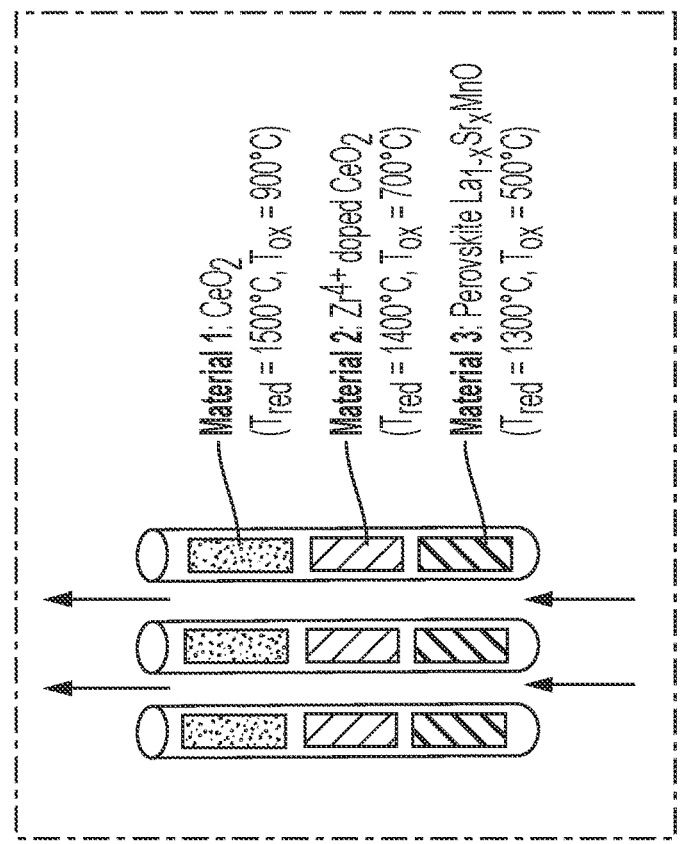
Figure 3B:
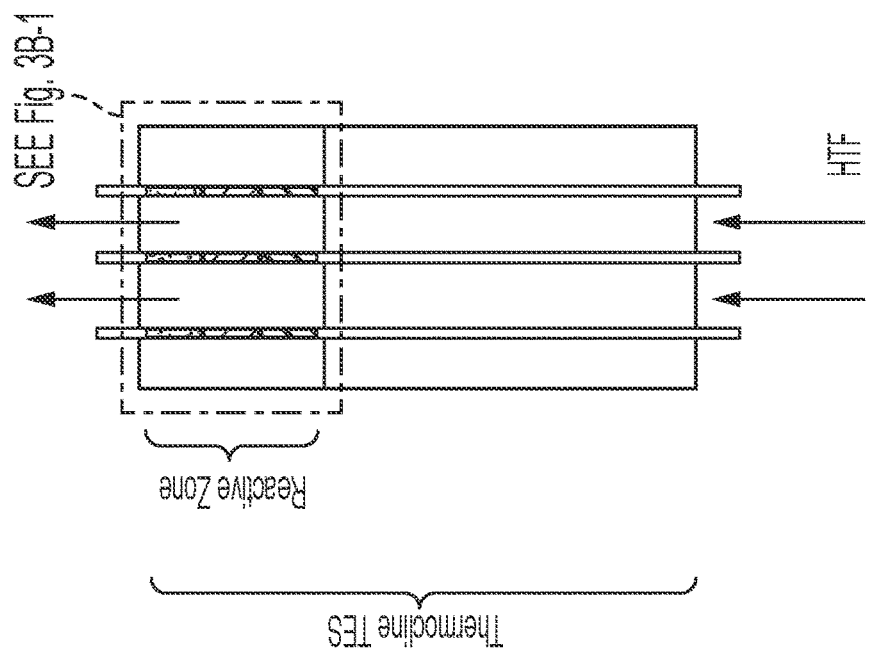
Figure 3C:
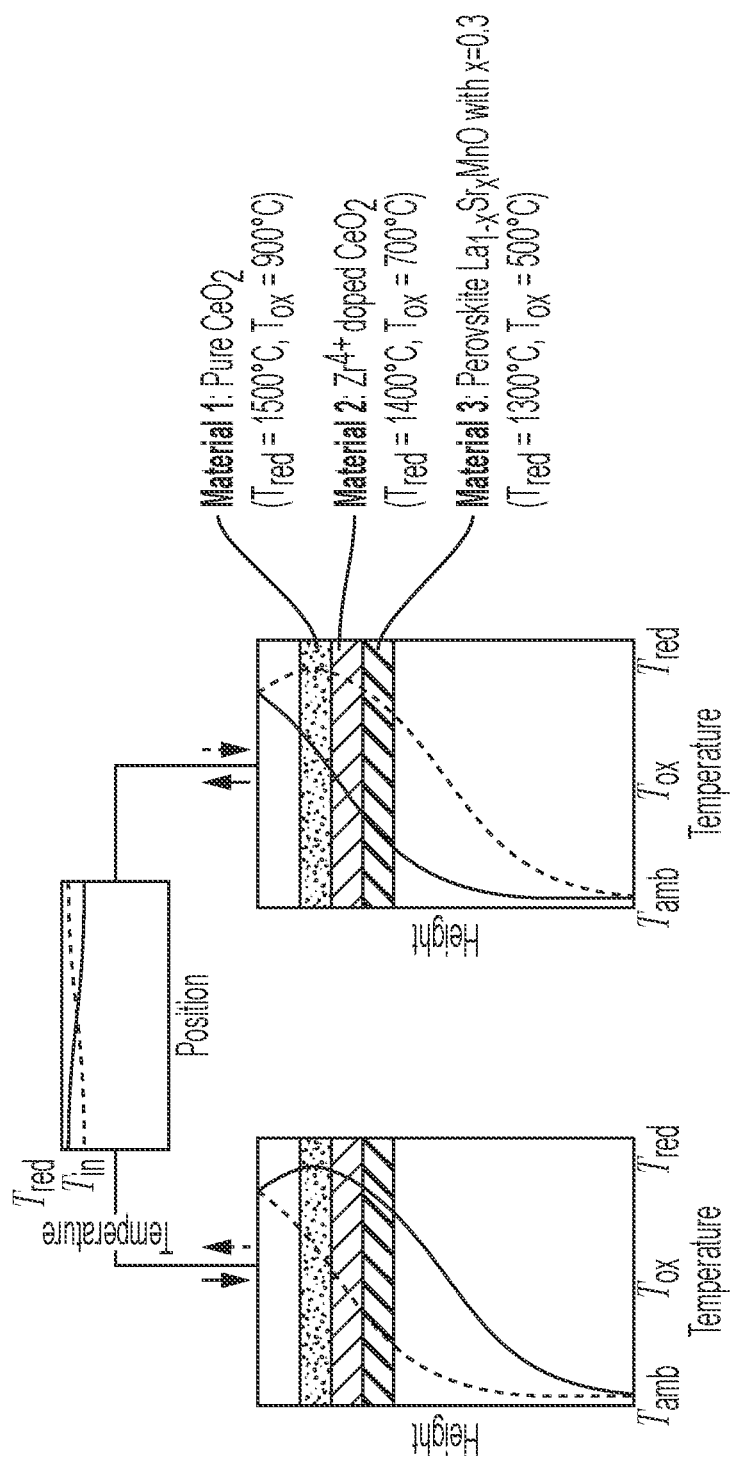
Figure 4A:
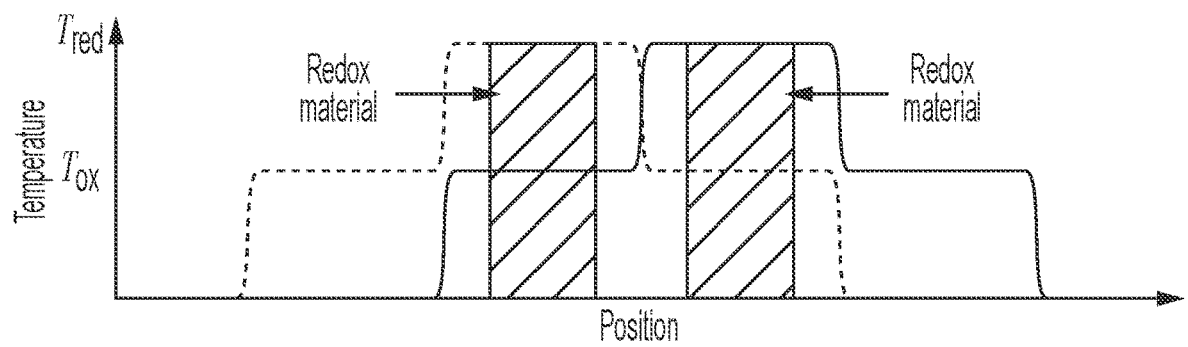
Figure 4B:
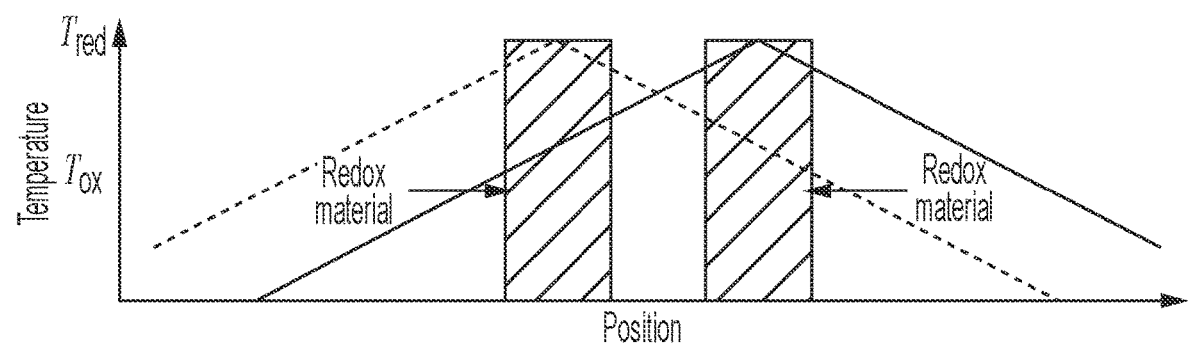
Figure 5A:
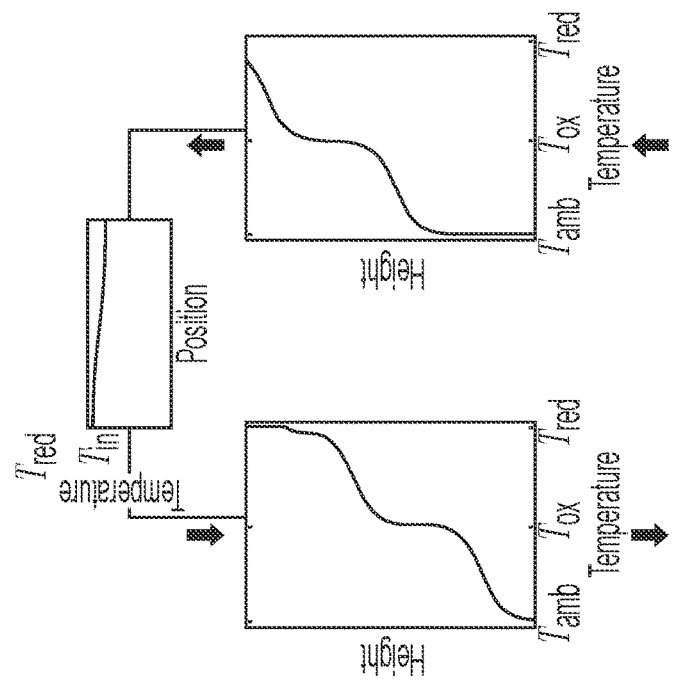
Figure 5A:
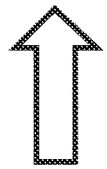
Figure 5A:
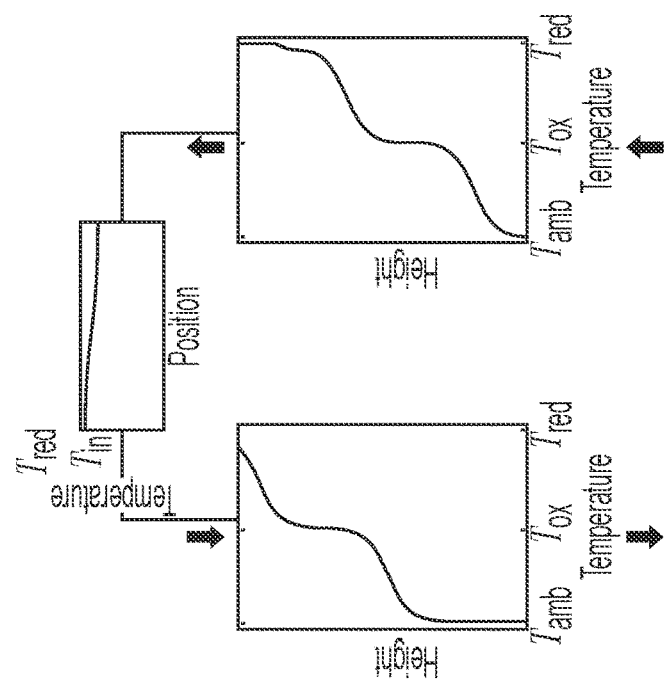
Figure 5B:
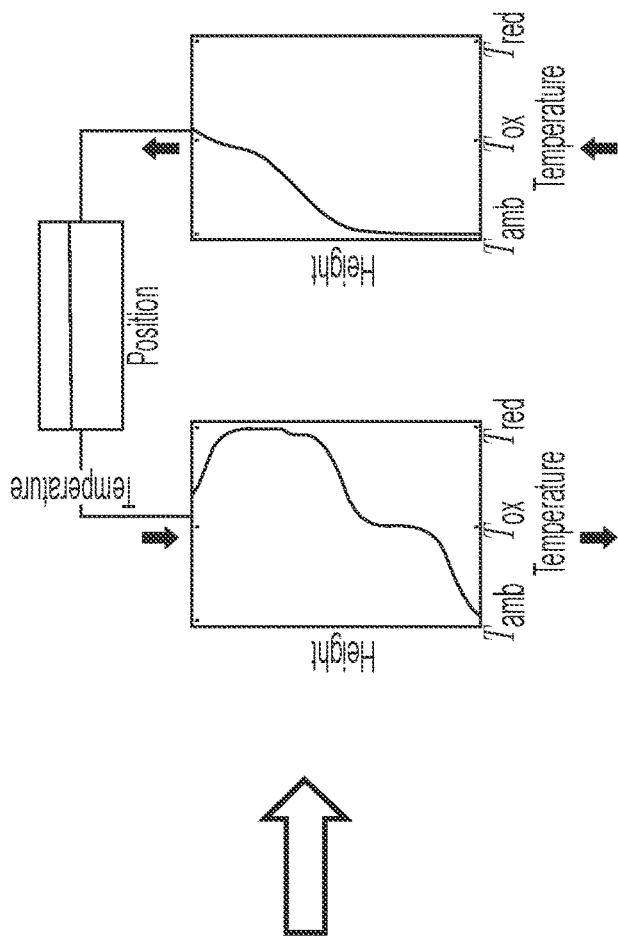
Figure 5B:
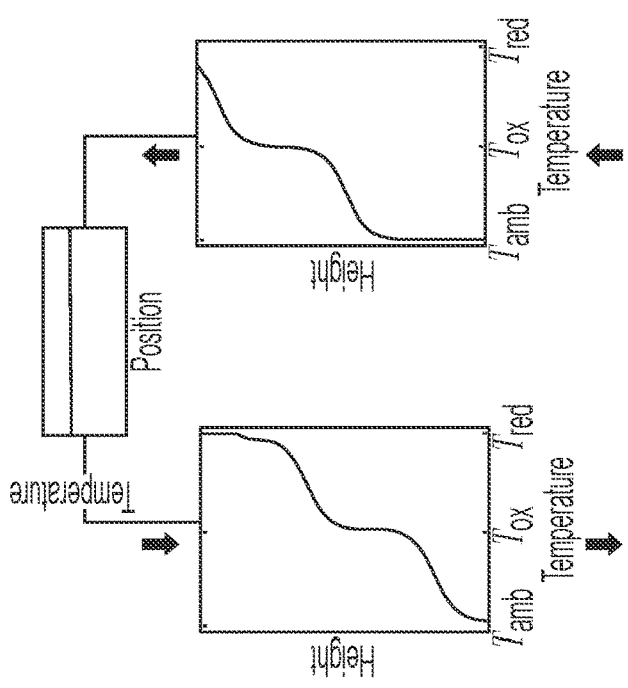
Figure 5C:
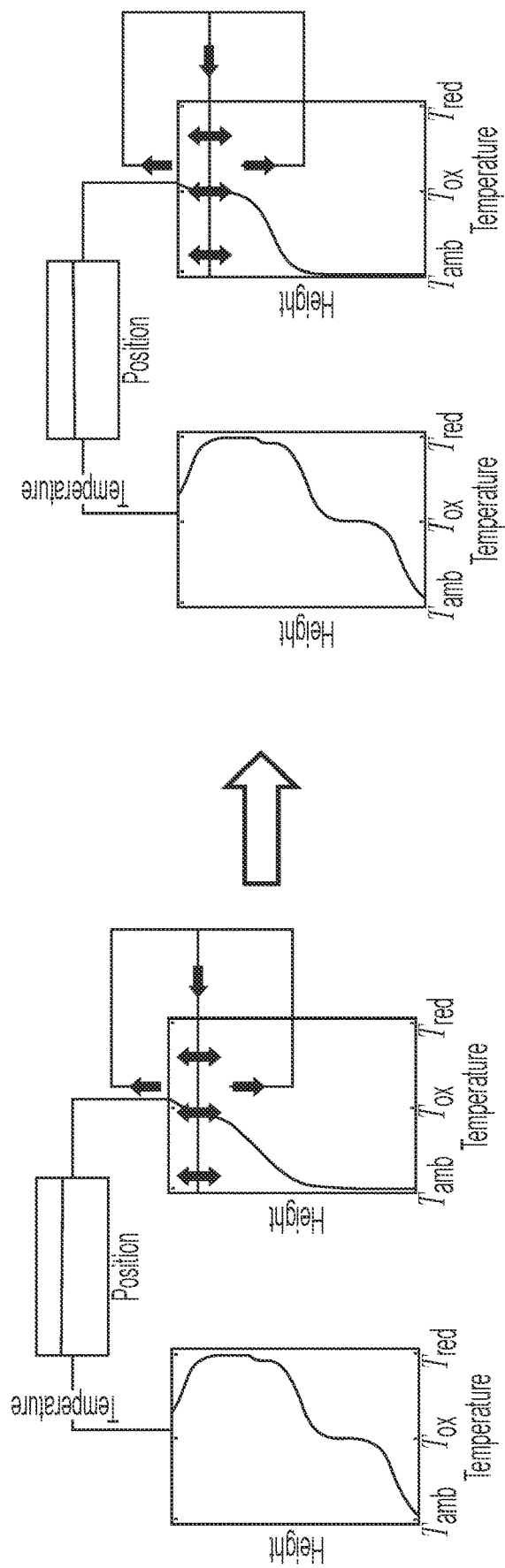
Figure 5D:
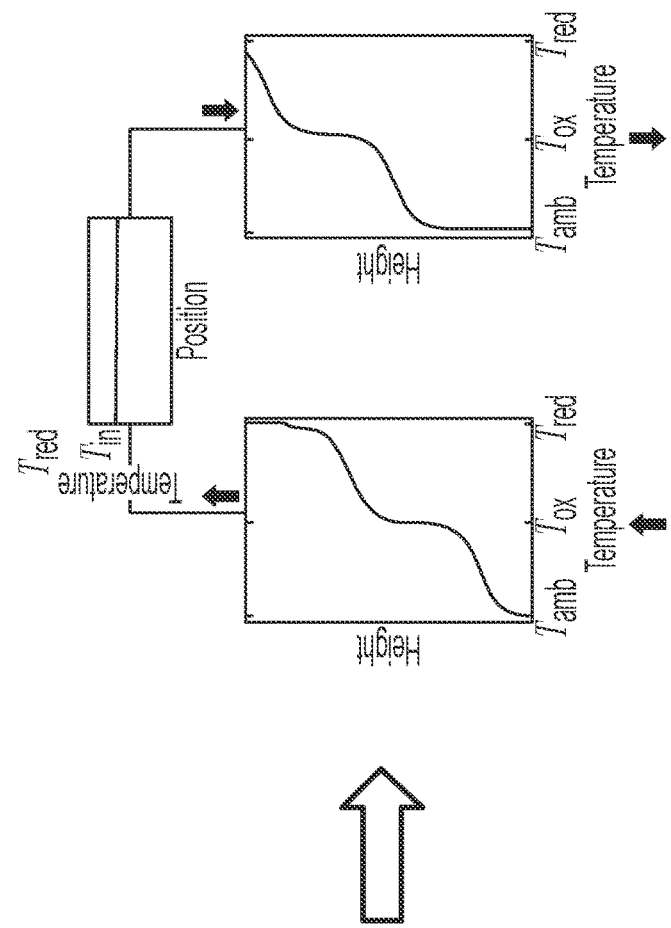
Figure 5D:
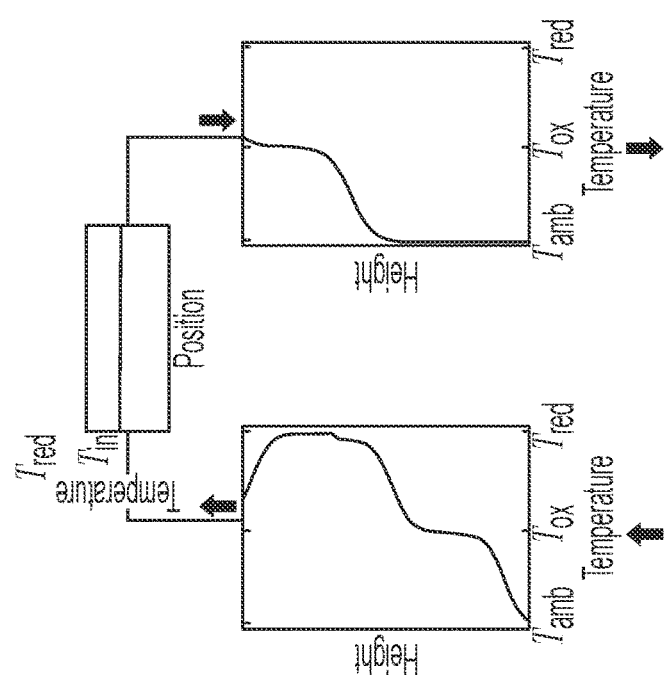
Figure 6A:
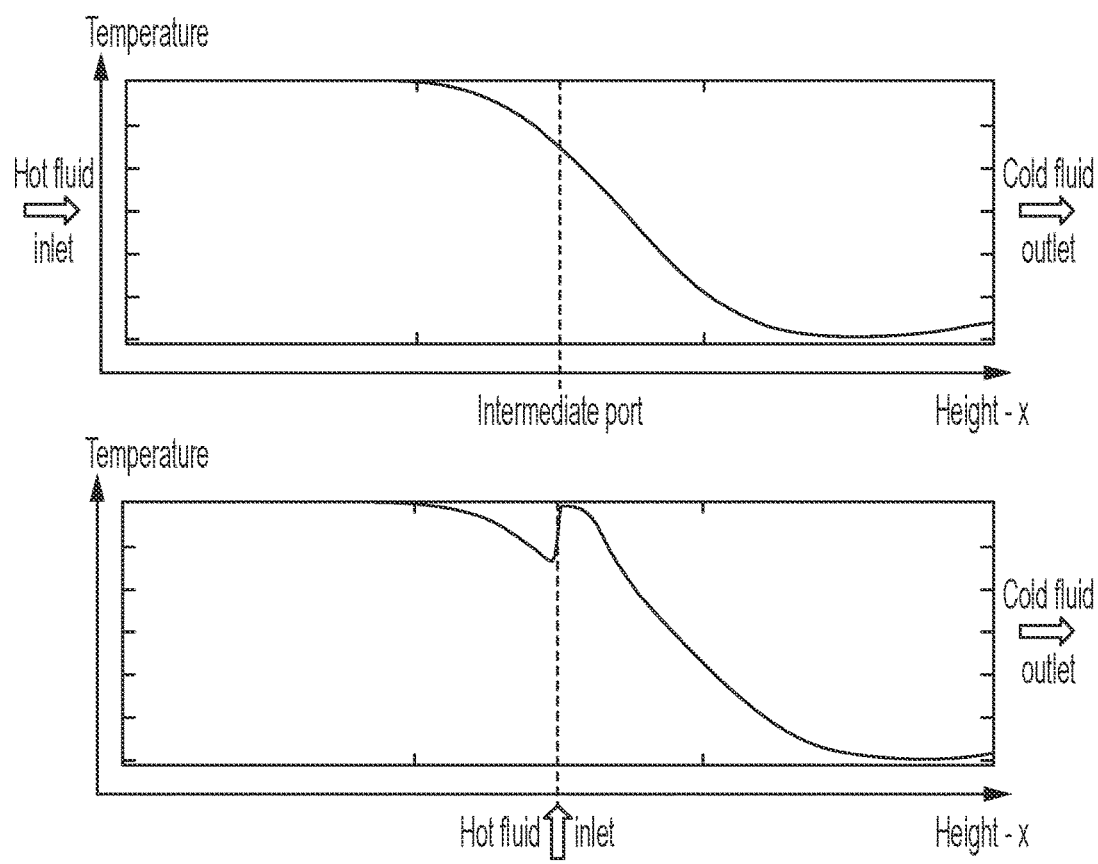

The invention is now explained in more detail with reference to the figures by means of an example. It shows:

FIG. 1 a scheme of a first embodiment of the present thermochemical reactor system;

FIG. 2a a scheme of a variant of an encapsulation of the reacting material perpendicular to the HTF flow direction;

FIG. 2b a scheme of further variants of an encapsulation of the reacting material;

FIG. 2c a scheme of yet further variants of an encapsulation of the reacting material;

FIG. 2d a scheme of a first variant of an encapsulation of the reacting material parallel to the HTF flow direction;

FIG. 2e a scheme of an encapsulation variant for redox material in syngas process;

FIG. 3a a scheme of a first cascaded encapsulation variant;

FIG. 3b a scheme of a second cascaded encapsulation variant;

FIG. 3c a scheme of a cascaded encapsulation variant for redox material in syngas process;

FIG. 4a an ideal temperature profile in a reactor system according to FIG. 1;

FIG. 4b a degraded temperature profile in a reactor system according to FIG. 1;

FIG. 5a Movement of temperature profile to bring the left tank to reduction temperatures;

FIG. 5b further moving of temperature profile without upgrading the compressed air in the CSP receiver;

FIG. 5c Thermocline control to obtain a uniform oxidation temperature plateau in the right redox zone;

FIG. 5d pushing back thermocline without upgrading;

FIG. 6a Temperature profile during charging process; and

Figure 6B:
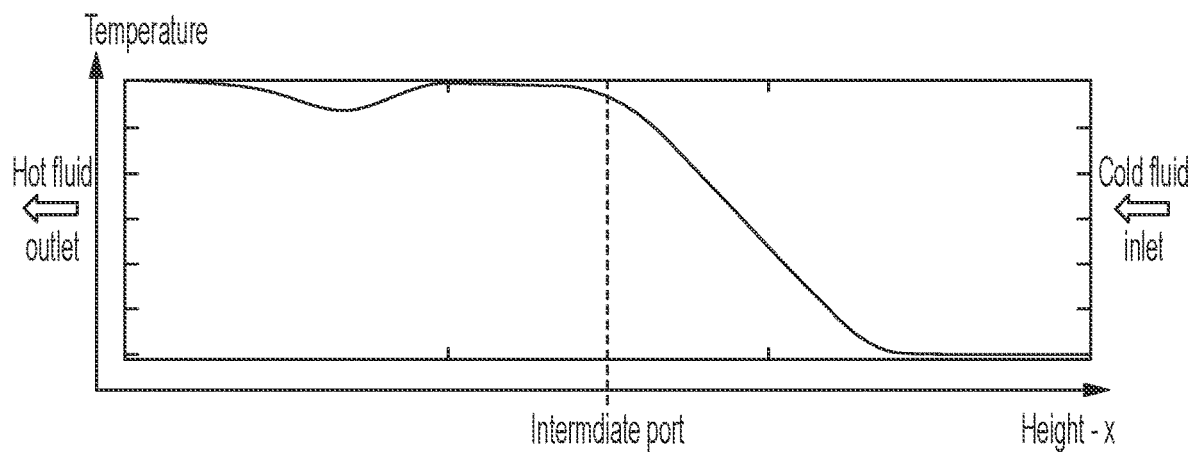

FIG. 6b Temperature profile during discharging process.

In FIG. 1 a first embodiment of the present reactor system in the form of a dual-storage reactor system is shown. The dual-storage reactor system consists of two vertically oriented thermal energy storage units (thermocline TES) such as packed beds of inert material. A chemical reaction zone (CRZ) comprising encapsulated redox material is placed on top of the thermocline TES, respectively. The packed beds serve as thermal energy storage (TES) units in which axial temperature gradients (thermoclines) are established.

The two combined CRZ/TES are operationally linked to each other by a heat transfer fluid (HTF) transporting heat through the system between both CRZ/TES units. A heating section for heating the HTF is provided between the two CRZ/TES such that the HTF heated in said heating section may flow into the CRT/TES, respectively.

By pumping HTF back and forth between the two CRZ/TES, the thermoclines in the CRZ/TES are shifted along the axial direction, and therefore the redox materials are alternately exposed to $T_{red}$ and $T_{ox}$. The sensible heat is thereby recuperated between the reduction and oxidation steps.

The flow direction of the HTF transporting the heat for the heating section to the chemical reaction zones and the thermal storage units is switched if the redox material in the one of the two chemical reaction zones operated at the reduction temperature $T_{red}$ of the redox material is reduced to a certain extent and/or if the redox material in the other chemical reaction zone operated at the oxidation temperature $T_{ox}$ of the redox material is oxidized back to a certain extent.

Process heat obtained by concentrated solar radiation is added to the HTF between the reaction zones to provide the reduction enthalpy and to compensate for thermal losses and thermocline degradation.

FIGS. 2a-2e illustrate certain variants of the encapsulation of the reacting material.

In FIG. 2a the reacting material is encapsulated in tubes which are arranged perpendicular to the flow direction of the heat transfer fluid within the chemical reaction zone. Thereby a variety of different arrangements of the encapsulations are possible. FIG. 2b illustrates some examples of possible arrangements; (a) parallel tube layers (bundles) with parallel stacking of the layers, (b) parallel tube layers with perpendicular stacking of the layers, (c) parallel tube layers with stacking of the layers in a certain angle (0-90 degree).

The reactive material can also be encapsulated in stacks similar to fuel-cell stacks. Thereby, the heat transfer fluid flows through dedicated channels while the reactive material is contained in separated chambers. Such arrangements are shown in FIG. 2c. The reactive material (e.g. $CeO_2$) is arranged in grooves or deepening within a block of inert encapsulation material (e.g. $Al_2O_3$). The HTF flows through channels in the inert encapsulation material, whereby grooves containing the reactive material and the HTF channels are arranged perpendicular to each other.

There may be more than one block or stack of inert encapsulation material, for example two or three blocks. In this case the blocks or stacks may be arranged parallel or perpendicular to each other.

The reacting material may also be encapsulated in tubes or stacks which are arranged parallel to the HTF flow direction (see FIG. 2d). Here, the encapsulation extends through the whole length of the TES but only contains the reacting material within the reactive zone. The remaining part of the tube or stack can be empty or filled with inert material. Again tube bundles or stacks could be used.

In FIG. 2e an encapsulation variant for redox material in syngas process is shown. Here the redox material is encapsulated in $Al_2O_3$ tubes. In each chemical reactor zone three tubes filled with the redox material are arranged parallel to each other. The tubes are placed within each chemical reaction zone perpendicular to the flow direction of HTF.

In this manner, direct contact between the HTF and redox material is avoided allowing the use of any suitable HTF. Furthermore, TES and CRZ can be operated at different pressures and gas atmospheres. For example, the TES units can be operated at $p>P_{ambient}$ (overpressure) to decrease the pumping work, while the CRZ can be operated at $p<p_{ambient}$ (vacuum) during thermal reduction and/or $p>p_{ambient}$ during oxidation to enhance the chemical reaction.

Each tube has a gas inlet and a gas outlet at the opposite ends allowing a gas flow through the tube and sufficient contact time of the reactants (such as $CO_2$, $H_2O$) with the redox material.

As depicted in FIG. 2e the left chemical reaction zone is operated at the reduction temperature $T_{red}$ of the redox material. In the course of the (endothermic) reduction of the redox material oxygen is released that is flushed out by feeding an inert gas into the encapsulation or extracted by applying a vacuum at the outlet.

The right chemical reaction zone is operated at the oxidation temperature $T_{ox}$ of the redox material. $CO_2/H_2O$ is fed into the redox material having $T_{ox}$ and is converted to $CO/H_2$ that is subsequently continuously discharged from the redox material in the tube. At the same time the reduced redox material is oxidized to its original state or a defined oxidation state in the course of the (exothermic) oxidation.

FIGS. 3a-c illustrate variants of a cascaded arrangement of the reacting material. Here instead of using a single reacting material multiple reacting materials that reduce and oxidize at different temperatures to create a cascaded dual-storage reactor are used.

In FIG. 3a the reacting materials are encapsulated in tubes or stacks to prevent direct contact of the heat transfer fluid and the reacting materials. Here, the different reacting materials are arranged along the height of the reactive zone, such that the different thermodynamic and kinetic properties of the individual materials, e.g. reduction and oxidation behavior, fit best the temperature distribution inside the chemical reaction zone. For example, in the top part of the chemical reaction zone where the highest temperatures are reached, a material with suitable thermodynamic and kinetic properties for these temperatures is selected, e.g., $CeO_2$. In lower levels of the reaction zone, where the temperatures are lower than in the top part, reacting materials with different thermodynamic and kinetic properties than in the top part are selected which operate favorably at these lower temperatures, e.g., doped $CeO_2$ or perovskites.

FIG. 3a shows schematically the arrangement of three different reacting materials for the case of parallel tube bundles arranged perpendicular to the flow direction of the heat transfer fluid. Similar arrangements can be achieved by stacks.

If the encapsulation is parallel to the flow direction of the heat transfer fluid, the different reacting materials can be layered within the same encapsulation such that again the material with the most appropriate thermodynamic and kinetic properties at the highest temperature is positioned in the hottest region while the one with the most appropriate thermodynamic and kinetic properties at lower temperatures is positioned in the region of the reactive zone where the lowest temperatures are obtained. FIG. 3b shows schematically the arrangement of three different reacting materials.

FIG. 3c shows such a cascaded arrangement suitable for syngas production. Here Redox Material 1 has the most appropriate thermodynamic and kinetic properties at the highest temperatures compared to the other redox materials such that; $T_{red/ox\_Material\ 1} > T_{red/ox\ Material\ 2} > T_{red/ox\ Material\ 3}$. Materials and corresponding optimal operation temperatures for this arrangement could be besides many possibilities.

In the embodiment of FIG. 3 a first layer comprises pure $CeO_2$; $T_{red}=1500°$ C., $T_{ox}=900°$ C. (material 1), the lower second layer comprises 5 mol % Zr4+ doped ceria; $T_{red}=1400°$ C., $T_{ox}=700°$ C. (material 2) and the lowest third layer comprises Lanthanum-strontium-manganese perovskite $La_{1-x}Sr_xMnO$ with x=0.3; $T_{red}=1300°$ C., $T_{ox}=500°$ C. (material 3).

FIGS. 4a, b illustrate the ideal and actual temperature profiles in a dual storage reactor, respectively.

The production of syngas with the dual-storage reactor is maximized if the redox material is always exposed to either the reduction or the oxidation temperature. This implies that near the reaction zone the temperature profile should ideally be a discontinuity separating two plateaus at the reduction and oxidation temperatures. Furthermore, a third plateau at a low temperature is desired because this reduces the cost of the pump that moves the HTF back and forth. To minimize the height and therefore the material cost of the packed beds, this third plateau should ideally be separated from the plateau at the oxidation temperature by a second discontinuity. Therefore, the complete ideal temperature profile—the so-called thermocline—in the dual-storage reactor is as shown in FIG. 4a.

However, the ideal temperature profile cannot be realized in practice because several physical mechanisms cause the discontinuities to become degraded, i.e., smeared (see FIG. 4b). These mechanisms include: limited heat-transfer rates between the HTF and the storage material, axial heat conduction and radiation along the storage, heat exchange with the storage container and insulation, mixing of the HTF at different temperatures due to vertical flows at the inlet and outlet and bypass flows at the container wall.

As the thermocline becomes more and more degraded, the production of syngas will decrease and there is a danger that the maximum operating temperature of the pump will be exceeded, requiring that the dual-storage reactor be shut down.

Actions taken to prevent degradation of the thermocline are usually referred to as "thermocline control". In the dual-storage reactor, thermocline control is partly achieved by the heating section because the heated HTF flows into a packed bed at a constant temperature equal to the reduction temperature.

To maintain a plateau at the oxidation temperature, however, thermocline control is necessary. This can be done in several ways: flushing the TES to push thermocline out of the storage, combination of different geometries/materials, e.g., combined sensible/latent-heat storage, extracting, upgrading, and returning the HTF at certain positions of the thermocline, siphoning HTF out of the TES at the location of the thermocline, and sliding flow (inlet and outlet moving with thermocline position).

Example 1

Description of the Dual-Storage Reactor Setup

The dual-storage reactor consists of two connected tanks each containing a section or module with a thermocline TES and a zone with redox material (as shown in FIG. 1).

In the reaction zones, alumina tube bundles are stacked, containing inside ceria as the reacting material (FIG. 2). The thermocline TES consist of packed beds of alumina spheres. The HTF is compressed air (e.g., at 20 bar). Pumping of the HTF is usually performed at the cold side. Concentrated solar radiation/energy is used to heat the HTF in a receiver (heating section).

To support the reduction of ceria, the tubes are flushed with inert gas while also a vacuum is pulled (left side of FIG. 2).

$$CeO_2 \rightarrow CeO_{2-\delta} + \frac{\delta}{2}O_2$$

During oxidation of ceria, $CO_2$ and $H_2O$ are injected into the tubes to produce syngas (right side of FIG. 2).

$$CeO_{2-\delta} + \delta H_2O \rightarrow CeO_2 + \delta H_2$$

$$CeO_{2-\delta} + \delta CO_2 \rightarrow CeO_2 + \delta CO$$

Operation Steps

In the following the individual steps of the operation are discussed separately. Since the two tanks are identical, for brevity only a half cycle is discussed. The second half of the cycle will then be identical to the first half, only that all operation actions are flipped between the left and the right tank.

At the beginning, the ceria of the left tank is in the oxidized state and the ceria of the right tank is in the reduced state. The following steps are performed in order to bring the ceria of the left tank in the reduced state and the ceria of the right tank in the oxidized state (and producing syngas).

First Step (FIG. 5a, FIG. 2e Left Side)

Compressed air is pumped from the bottom of the right tank through the right tank, and is then upgraded by a concentrated solar radiation receiver to the desired reduction temperature ($T_{red}$=1500° C.). The HTF mass flow rate may be adjusted to obtain the desired reduction temperature, depending on the momentary direct normal irradiation (DNI) and the inlet temperature into the receiver. The upgraded compressed air enters then the left tank and leaves it at the bottom as cold compressed air (FIG. 5a). In this way, the high temperature plateau of the right tank is moved from the right tank to the left tank.

Simultaneous (perpendicular) flow inside tubes containing ceria: Inside the tubes of the right tank, there is no flow. In the tubes of the left tank, a small flow of inert gas is injected and the total pressure is reduced (e.g. to 10 Pa) by pulling a vacuum, see FIG. 2e, left side.

Second Step (FIG. 5b)

Once the ceria of the left tank is reduced, the redox material of the right tank is usually not yet at oxidation temperatures but at somewhat higher temperatures due to limited thermocline steepness (see FIG. 5a). To further cool down and to prevent spreading of the high temperature plateau (at ~$T_{red}$), the hot compressed air leaving the right tank can be directed to the left tank without upgrading it with solar energy, resulting in the temperature profiles shown schematically in FIG. 5b. In this way, heat is still recuperated but no spreading of the thermocline occurs.

Inside the right tubes there is again no flow while in the left tank vacuum is still pulled to increase the reduction extent (FIG. 2e, left side).

Third Step (FIG. 5c)

Due to thermocline degradation, the temperature plateaus degrade over time. To reestablish the plateaus, thermocline control is needed. In order to obtain a uniform oxidation temperature in the redox zone of the right tank, compressed air is extracted at the top and at the bottom of the right reaction zone and its mixture is injected in the middle of the right reaction zone (FIG. 5c).

Fourth Step (FIG. 2e, Right Side)

$CO_2$ and $H_2O$ are injected into the tubes of the right redox section to oxidize the ceria and produce syngas (FIG. 2e, right side).

Fifth Step (FIG. 5d)

After oxidation of the right redox zone, compressed air is pumped from the bottom of the left tank through the right tank, and then without upgrading it with solar energy, it enters the right tank and leaves it at the bottom as cold compressed air (FIG. 5d). In this way, heat is still recuperated but no spreading of the thermocline occurs.

At the end of the fifth step, the temperature distribution is the same as at the beginning of step one, just with the distributions flipped between the left and the right tank. Hence the next half of the cycle will be the same procedure, just with all actions flipped between the two tanks.

Example 2: Temperature Profile (Thermocline Control)

According to an embodiment of the present method HTF is injected ahead of thermocline.

Several additional ports are placed inside the TES. The thermocline is then steepened by injecting fluid ahead of the thermocline front based on certain criteria.

An example of this method applied during the charging phase can be seen in FIG. 6a. Here the inlet port is switched before the whole thermocline region has passed the respective port. This leads to a cut-off of the thermocline, entrapping a portion of the thermocline within the storage tank while the charging continues between the new inlet port and the outlet port with a steeper thermocline.

During the following discharging, the entrapped portion of the thermocline is flattened out due to dispersion effects (axial conduction, limited convective heat transfer) and gets then pushed out of the tank (FIG. 6b). The analogous injection strategy can be performed during charging.

It is also possible, that more TC control strategies may be used for this example, such as:

Pushing out of the thermocline at medium-high temperatures: Due to the heat of oxidation which is produced during oxidation, excess heat might be present at ~$T_{ox}$. This heat needs to be extracted in order to prevent a continuous temperature increase in the two tanks, making re-oxidation more and more difficult. This can be done, for example, by extracting part of the thermocline at the end of the second step by injecting compressed air at the bottom of the left tank and extracting compressed air at the top of it at around $T_{ox}$. This heat could be used e.g. to run a turbine for electricity production.

Instead of performing step two, one could extract fluid from (approximately) the middle of the right tank and insert it into the left tank to bring the left tank to oxidation temperatures. This would avoid moving of the whole temperature profile. After oxidation of the left tank, the same amount of fluid would then be returned from the left tank top to the middle of the right tank.

Instead of mixing fluids in the reaction zone (step three), the mixing to obtain a plateau at $T_{ox}$ could be performed in the thermocline TES (e.g. at the beginning of step one). This would have the advantage, that the flow distributors inside the tanks would not have to be made out of ceramic but could be made out of steel.

Different mixing/extracting/injecting possibilities exist to increase the steepness of the temperature gradients, such as siphoning.

The invention claimed is:

1. A thermochemical reactor system for a temperature swing cyclic process with integrated heat recovery comprising:
   at least two modules, wherein each module comprises at least one chemical reaction zone (CRZ) and at least one thermal energy storage unit (TES);
   wherein the at least two modules are operationally connected for at least one heat transfer fluid (HTF) for transporting heat between the two modules;
   wherein each chemical reaction zone (CRZ) comprises at least one reacting material that undergoes in a reversible manner an endothermic reaction at temperature $T_{endo}$ and an exothermic reaction at temperature $T_{exo}$, wherein $T_{endo}$ and $T_{exo}$ differ from each other;
   wherein the at least one reacting material is provided in at least one encapsulation within each of the chemical reaction zones (CRZ) such that a contact of the reacting material and the at least one heat transfer fluid is avoided.

2. The reactor system according to claim 1, wherein the at least one reacting material in each chemical reaction zone is at least one metal oxide undergoing reduction at reduction temperature $T_{red}$ and oxidation at oxidation temperature $T_{ox}$, wherein $T_{red}$ and $T_{ox}$ differ from each other.

3. The reactor system according to claim 1, wherein the at least one reacting material in each chemical reaction zone is at least one material undergoing adsorption at adsorption temperature $T_{adsorp}$ and desorption at desorption temperature $T_{desorb}$ of at least one compound.

4. The reactor system according to claim 1, wherein the at least one reacting material in each chemical reaction zone is at least one material undergoing carbonation by reacting with CO2 at carbonation temperature $T_{carb}$ and de-carbonation by releasing $CO_2$ at de-carbonation temperature $T_{decarb}$ of at least one compound, wherein $T_{carb}$ and $T_{decarb}$ differ from each other.

5. The reactor system according to claim 1, wherein each chemical reaction zone is arranged adjacent to the corresponding thermal energy storage unit (TES).

6. The reactor system according to claim 1, wherein the at least one encapsulation containing the reacting material is arranged perpendicular, parallel or in any other angle to the flow direction of the HTF through the at least one chemical reaction zone.

7. The reactor system according to claim 1, wherein the at least one encapsulation is provided in form of at least one tube, a tube bundle or a chamber.

8. The reactor system according to claim 1, wherein the reacting material is provided in at least two encapsulations.

9. The reactor system according to claim 8, wherein the encapsulations are arranged parallel and/or perpendicular to each other.

10. The reactor system according to claim 1, wherein the encapsulation is made of a material with a good thermal conductivity.

11. The reactor system according to claim 1, wherein at least two reacting materials with different reduction/oxidation temperatures or different adsorption/desorption temperatures or different carbonation/decarbonation temperatures are used, wherein the different reacting materials are arranged in series along the flow direction of the HTF.

12. The reactor system according to claim 11, wherein each of the different reacting material is arranged in a tube or stack such that a temperature gradient is created between the different reacting materials.

13. The reactor system according to claim 1, wherein the thermal energy storage units store thermal energy in the form of sensible heat (SHS) and/or latent heat (LHS), and/or heat of reaction of reversible thermochemical reactions (TCS).

14. The reactor system according to claim 1, wherein the thermal energy storage units comprise a heat storage material comprising a porous structure made of a ceramic material in the form of bricks, channels, pellets, or spheres made of zirconia, silica, or alumina.

15. The reactor system according to claim 1, wherein the reactor system is coupled to at least one external source of thermal energy (ESE) for heating the HTF.

16. The reactor system according to claim 15, wherein the external source of thermal energy obtains process heat from a solar receiver and/or electrical heating elements and/or plasma torches and/or combustion of fuels.

17. The reactor system according to claim 1, wherein the heat transfer fluid (HTF) is air, carbon dioxide, helium, steam, molten salt, molten metals, molten glass, nitrogen, argon, synthetic oils.

18. A method for operating the reactor system according to claim 1, wherein one of the two chemical reaction zones is operated at the temperature $T_{endo}$ of the endothermic reaction and the other chemical reaction zone is operated at the temperature $T_{exo}$ of the exothermic reaction of the reacting material, wherein the heat required for the chemical reaction zones is provided by a heat transfer fluid.

19. The method according to claim 18, wherein one of the two chemical reaction zones is operated at the reduction temperature $T_{red}$ and the other chemical reaction zone is operated at the oxidation temperature T0x of a metal oxide used as reacting material.

20. The method according to claim 19, wherein the metal oxide as reacting material is used for converting water and carbon dioxide to syngas comprising hydrogen and carbon monoxide or for converting methane, water, and carbon dioxide to syngas comprising hydrogen and carbon monoxide.

21. The method according to claim 19, wherein the metal oxide as reacting material is used for converting water and carbon dioxide to hydrocarbons.

22. The method according to claim 19, wherein the metal oxide as reacting material is used for the separation of oxygen from air or from any other gas mixtures.

23. The method according to claim 18, wherein one of the two chemical reaction zones is operated at the adsorption temperature $T_{adsorp}$ and the other chemical reaction zone is operated at the desorption temperature $T_{desorb}$ of the reacting material.

24. The method according to claim 23, wherein the adsorbing/desorbing reacting material is used for the separation of carbon dioxide and/or water from air or from any other gas mixtures containing any of these compounds.

25. The method according to claim 18, wherein one of the two chemical reaction zones is operated at the carbonation temperature $T_{carb}$ and the other chemical reaction zone is operated at the decarbonation temperature $T_{decarb}$ of the reacting material.

26. The method according to claim 25, wherein the carbonation/decarbonation reacting material is used for the separation of carbon dioxide from gas mixtures containing any of these compounds.

27. The method according to claim 18, wherein the heat transfer fluid is heated by the external source of thermal energy.

28. The method according to claim 18, wherein the temperature and temperature profile (thermocline) of the chemical reaction zones is additionally controlled and maintained by extracting, heating and injecting the heated heat transfer fluid at different positions along the chemical reaction zones and/or the thermal energy storage units.

29. The method according to claim 18, wherein the temperature and temperature profile of the chemical reaction zones is additionally controlled and maintained by extracting HTF from any position of the TES unit to transport the stored heat into the respective chemical reaction zone.

30. The method according to claim 18, wherein the temperature profile is controlled by having multiple ports along the modules for extraction and injection of HTF.

31. The method according to claim 18, wherein the temperature profile inside at least one module is steepened by injecting HTF at an intermediate position of the temperature profile cutting off a certain portion of the temperature profile.

32. The method according to claim 31, wherein the criteria for switching the HTF injection port is determined based on comparing the actual stored energy between two ports and a target/reference energy.

33. The method according to claim 18, wherein the temperature profile is controlled by extracting HTF at one port of a module and injecting it back at another port of a module.

34. The reactor system according to claim 3, wherein that at least one material is at least one gas.

35. The reactor system according to claim 3, wherein the at least one gas is $CO_2$.

36. The reactor system according to claim 8, wherein the reacting material is provided in three or more encapsulations.

37. The reactor system according to claim 10, wherein the material is at least one of aluminum, silicon carbide, or high-temperature alloys.

38. The method according to claim 21, wherein the hydrocarbons comprise $CH_4$.

* * * * *